US010370647B2

(12) United States Patent
Nakamura et al.

(10) Patent No.: US 10,370,647 B2
(45) Date of Patent: Aug. 6, 2019

(54) HOST REGULATORY FACTOR THAT ENHANCES REPLICATION AND/OR PROPAGATION OF VACCINIA VIRUS

(71) Applicant: National University Corporation Tottori University, Tottori-shi, Tottori (JP)

(72) Inventors: Takafumi Nakamura, Yonago (JP); Kousuke Horita, Yonago (JP); Hajime Kurosaki, Yonago (JP); Motomu Nakatake, Yonago (JP)

(73) Assignee: National University Corporation Tottori University, Tottori-shi, Tottori (JP)

( * ) Notice: Subject to any disclaimer, the term of this patent is extended or adjusted under 35 U.S.C. 154(b) by 0 days.

(21) Appl. No.: 15/746,018

(22) PCT Filed: Jul. 22, 2016

(86) PCT No.: PCT/JP2016/071538
§ 371 (c)(1),
(2) Date: Jan. 19, 2018

(87) PCT Pub. No.: WO2017/014296
PCT Pub. Date: Jan. 26, 2017

(65) Prior Publication Data
US 2018/0208904 A1 Jul. 26, 2018

(30) Foreign Application Priority Data
Jul. 22, 2015 (JP) ................................ 2015-145153

(51) Int. Cl.

| | |
|---|---|
| *C12N 7/00* | (2006.01) |
| *C12N 7/04* | (2006.01) |
| *A61K 35/76* | (2015.01) |
| *A61P 35/00* | (2006.01) |
| *C12N 15/09* | (2006.01) |
| *G01N 33/53* | (2006.01) |
| *A61K 35/768* | (2015.01) |
| *C12Q 1/6886* | (2018.01) |
| *G01N 33/574* | (2006.01) |

(52) U.S. Cl.
CPC ................ *C12N 7/00* (2013.01); *A61K 35/76* (2013.01); *A61K 35/768* (2013.01); *A61P 35/00* (2018.01); *C12N 7/04* (2013.01); *C12N 15/09* (2013.01); *C12Q 1/6886* (2013.01); *G01N 33/53* (2013.01); *G01N 33/574* (2013.01); *C12N 2710/24132* (2013.01); *C12Q 2600/106* (2013.01); *C12Q 2600/158* (2013.01)

(58) Field of Classification Search
CPC C12N 7/00; C12N 2710/24132; C12N 15/09; C12N 7/04; C12Q 1/6886; C12Q 2600/158; C12Q 2600/106; G01N 33/574; G01N 33/53; A61P 35/00; A61K 35/76; A61K 35/768
See application file for complete search history.

(56) References Cited

U.S. PATENT DOCUMENTS

2013/0071430 A1 3/2013 Nakamura et al.
2016/0281066 A1 9/2016 Nakamura

FOREIGN PATENT DOCUMENTS

WO 2011/125469 10/2011
WO WO-2013033609 A2 * 3/2013 ....... G01N 33/57484
WO 2015/076422 5/2015

OTHER PUBLICATIONS

Thorne SH. "Chapter 32: Design and Testing of Novel Oncolytic Vaccinia Strains." In: Methods in Molecular Biology, Gene Therapy of Cancer. 2nd Ed., vol. 542. Walther W and Stein US, eds. pp. 635-648. 2009.*
Wang, Fang, et al., "Upregulated IncRNA-UCA1 contributes to progression of hepatocellular carcinoma through inhibition of MiR-216b and activation of FGFR1/ERK signaling pathway", Feb. 11, 2015, Oncotarget, vol. 6, No. 10, pp. 7899-7917.
Liu, Shi-Ping, et al., "Identification of Differentially Expressed Long Non-Coding RNAs in Human Ovarian Cancer Cells with Different Metastatic Potentials", Sep. 2013, Cancer Biology & Medicine, vol. 10, No. 3, pp. 138-141.
Zheng, Q., et al., "Aberrant Expression of UCA1 in Gastric Cancer and Its Clinical Significance", Apr. 24, 2015, Clinical and Translational Oncology, pp. 1-7.
Wang, Xiao-Song, et al., "Rapid Identification of UCA1 as a Very Sensitive and Specific Unique Marker for Human Bladder Carcinoma", Aug. 15, 2006, Clinical Cancer Research, vol. 12, No. 16, pp. 4851-4858.
European Search Repoted dated Feb. 12, 2019, based on co-pending European Application No. 16827856.2—6 Pages.
Zioza, Andrew, et al., "Immunoglobulin-like Transcript 2 (ILT2) is a Biomarker of Therapeutic Response to Oncolytic Immunotherapy with Vaccinia Viruses", Journal of ImmunoTherapy of Cancer, Jan. 27, 2014, vol. 2, No. 1, pp. 1-8.
Breiman, Adrien, et al., "Vaccinia Virus B5 Protein Affects the Glycosylation, Localization and Stability of the A34 Protein", 2010, Journal of General Virology, vol. 91, pp. 1823-1827.

(Continued)

*Primary Examiner* — Rachel B Gill
(74) *Attorney, Agent, or Firm* — McCarter & English, LLP

(57) ABSTRACT

It is an object of the present invention to provide utilization of a UCA1 gene that is a host regulatory factor that enhances replication and/or propagation of a vaccinia virus, in order to effectively carry out cancer virotherapy using the vaccinia virus. The present invention relates to: a method for predicting and evaluating the cancer therapeutic effects of a vaccinia virus, which comprises measuring the expression of a UCA1 gene in the cancer cells of a cancer patient, and then predicting that a vaccinia virus exhibits cancer therapeutic effects on the patient, when the UCA1 gene has been expressed therein; and a vaccinia virus into which a UCA1 gene has been expressibly introduced.

7 Claims, 28 Drawing Sheets

Specification includes a Sequence Listing.

(56) References Cited

OTHER PUBLICATIONS

Humphries, Ashley C., et al., "Cdc42 and the Rho GEF intersectin-1 collaborate with Nck to promote N-WASP-dependent actin polymerisation", 2014, Journal of Cell Science vol. 127, pp. 673-685.

Miki, Hiroaki, et al., "Induction of filopodium formation by a WASP-related actin-depolymerizing protein N-WASP", Jan. 1, 1998, Nature, vol. 391, pp. 93-96.

Zhong, Peng, et al., "Cell-to-Cell Transmission of Viruses", Feb. 2013, Current Opinion in Virology, vol. 3, No. 1, pp. 1-13.

Wang, Yu, et al., "Long non-coding RNA UCA1a(CUDR) promotes proliferation and tumorigenesis of bladder cancer", 2012, International Journal of Oncology, vol. 41, pp. 276-284.

Liu, Fang-Teng, et al., "The prognostic significance of UCA1 for predicting clinical outcome in patients with digestive malignancies", 2017, Oncotarget, vol. 8, (No. 25), pp. 40620-40632.

Bian, Zehua, et al., LncRNA-UCA1 enhances cell proliferation and 5-fluorouracil resistance in colorectal cancer by inhibiting miR-204-5p, Scientific Reports, vol. 6, pp. 1-12.

Liu, Hongying, et al., "Knockdown of Long Non-Coding RNA UCA1 Increases the Tamoxifen Sensitivity of Breast Cancer Cells through Inhibition of Wnt/β-Catenin Pathway", Dec. 15, 2016, PLOS One, vol. 11, pp. 1-14.

Andrade, Anderson A. et al., "The vaccinia virus-stimulated mitogen-activated protein kinase (MAPK) pathway is required for virus multiplication", 2004, Biochemical Journal, vol. 381, pp. 437-446.

Zloza, Andrew, et al., "Immunoglobulin-like Transcript 2 (ILT2) is a Biomarker of Therapeutic Response to Oncolytic Immunotherapy with Vaccinia Viruses", Journal of ImmunoTherapy of Cancer, Jan. 27, 2014, vol. 2, No. 1, pp. 1-8.

\* cited by examiner

Fig. 1

KFtx —Culture without PTx→ Low ⇄ (Co-culture with PTx / Culture without PTx) Reversible ⇄ LowTx Reduction in PTx resistance properties Recovery of PTx resistance properties

Fig. 2

(a) Structure of virus

LC16mO(O1L+/VGF+)

HA

EGFP Luciferase

LC16mO/VGF-O1L-(O1L-/VGF-)

VGF   O1L

DsRed (b)

KFtx    LowTx    Low

High ⟵ Low

Anticancer drug resistance properties

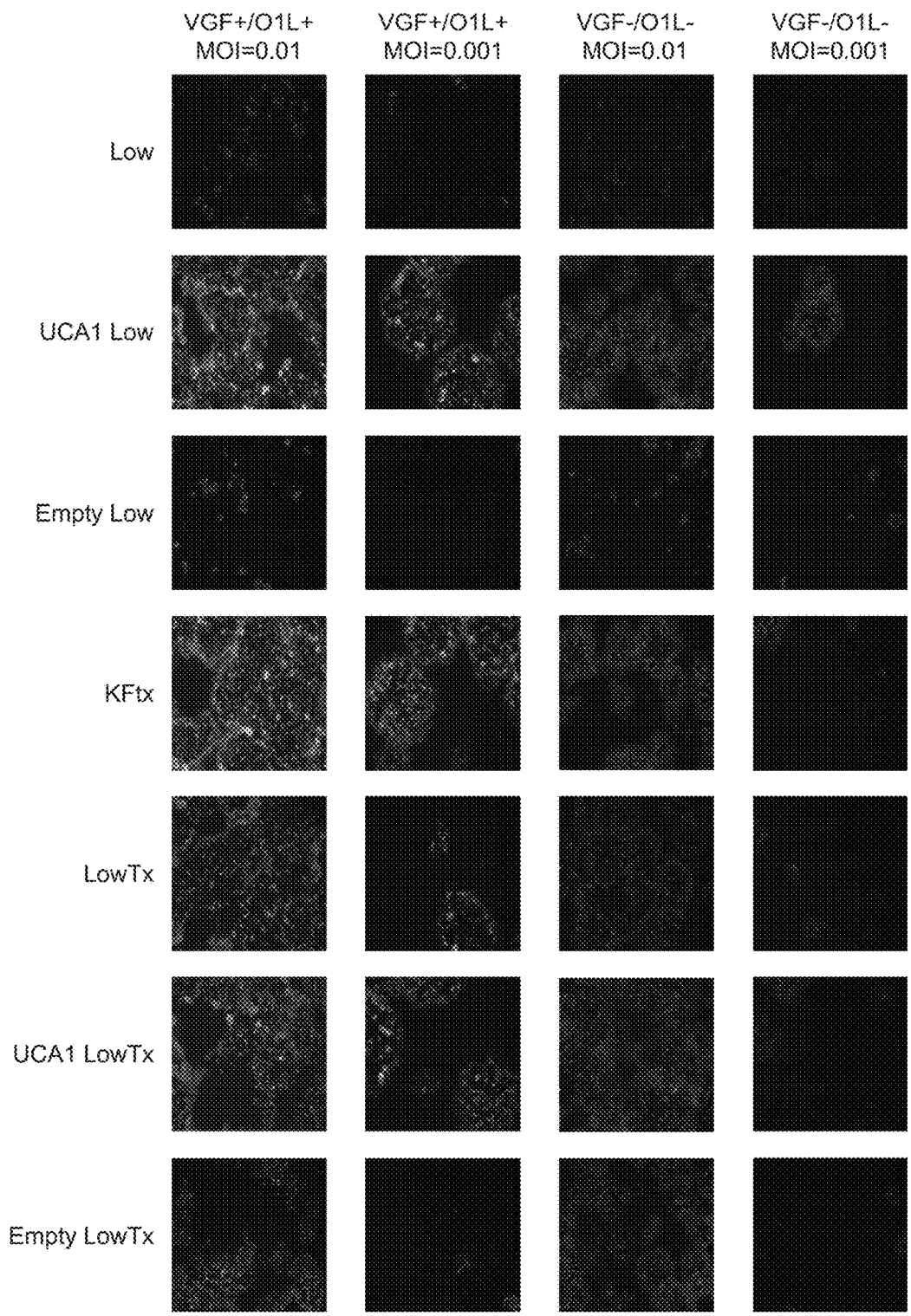

(a)

(b)

(a)

(b)

HOST REGULATORY FACTOR THAT ENHANCES REPLICATION AND/OR PROPAGATION OF VACCINIA VIRUS

CROSS-REFERENCE TO RELATED APPLICATIONS

This application is a national stage application filed under 35 USC 371 of PCT/JP2016/071538, filed Jul. 22, 2016, which claims the benefit of Japanese Patent Application No. 2015-145153, filed Jul. 22, 2015, each of which is incorporated herein, in its entirety, by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 119244_00127_Sequence_Listing. The size of the text file is 8 KB, and the text file was created on Jan. 17, 2018.

TECHNICAL FIELD

The present invention relates to a host regulatory factor that enhances replication and/or propagation of a vaccinia virus, which is used in cancer virotherapy using the vaccinia virus.

BACKGROUND ART

In recent years, various techniques relating to cancer virotherapy involving the use of viruses in cancer therapy have been developed. Viruses used in such therapy include vaccinia virus, as well as adenovirus and retrovirus.

In recent years, vaccinia virus has also been used as a multivalent vaccine for infections (HIV or SARS) in the form of an expression vector into which a foreign gene has been introduced, since the vaccinia virus has properties such as a wide range of hosts and high expression efficiency.

Moreover, a technique of utilizing the dissolving ability of vaccinia virus on cancer cells, so that the vaccinia virus can be utilized in cancer therapy, has been reported (see Patent Literature 1 and Patent Literature 2).

UCA1 has been reported as a gene associated with tumorigenesis or embryogenesis (see Non Patent Literature 1 to Non Patent Literature 4). It has been reported that a UCA1 (Urothelial cancer associated 1) gene is long-non coding RNA (lncRNA) that does not encode a protein, and that this gene is used as a marker for bladder cancer and the like.

CITATION LIST

Patent Literature

Patent Literature 1: International Publication WO 2011/125469

Patent Literature 2: International Publication WO 2015/076422

Non Patent Literature

Non Patent Literature 1: Wang F et al., Oncotarget, 2015, Apr. 10; 6(10): 7899-7917

Non Patent Literature 2: Shi-Ping Liu et al., Cancer Biol Med., 2013 September; 10(3): 138-141

Non Patent Literature 3: Zheng Q et al., Clin Transl Oncol., 2015 August; 17(8): 640-646

Non Patent Literature 4: Wang X S et al., Clin Cancer Res., 2006 Aug. 15; 12(16): 4851-4858

SUMMARY OF INVENTION

Technical Problem

It is an object of the present invention to provide utilization of a UCA1 gene that is a host regulatory factor enhancing replication and/or propagation of a vaccinia virus, in order to effectively carry out cancer virotherapy using the vaccinia virus.

Solution to Problem

The present inventor has conducted studies regarding the relationship between the resistance of an ovarian cancer cell line, KF cells, to anticancer drugs, and replication of a vaccinia virus. As a result, the inventor has found that the level of the anticancer drug resistance properties correlates with the degree of replication of the vaccinia virus, in cells having high anticancer drug resistance properties, cells having moderate anticancer drug resistance properties, and cells having no anticancer drug resistance properties.

The present inventor has conducted a comprehensive gene analysis using a microarray, so that the inventor has identified a UCA1 gene that is long-non coding RNA (lncRNA) as a factor for regulating replication of a vaccinia virus in cancer cells.

Based on the obtained findings, the inventor has found that the cancer virotherapeutic effects of the vaccinia virus can be predicted and evaluated based on the expression level of the UCA1 gene in the cancer cells of a cancer patient, and that the cancer virotherapeutic effects of the vaccinia virus on the cancer cells can be enhanced by allowing the UCA1 gene to express in the cancer cells, thereby completing the present invention.

Specifically, the present invention is as follows.

[1] A method for predicting and evaluating the cancer therapeutic effects of a vaccinia virus, which comprises measuring the expression of a UCA1 gene in the cancer cells of a cancer patient, and then predicting that a vaccinia virus exhibits cancer therapeutic effects on the patient, when the UCA1 gene has been expressed therein.

[2] The method according to the above [1], wherein the vaccinia virus is an oncolytic vaccinia virus.

[3] The method according to the above [1] or [2], wherein the vaccinia virus is an LC16 strain, an LC16mO strain, or an LC16m8 strain modified to allow the expression of a B5R gene.

[4] The method according to any one of the above [1] to [3], wherein the expression of the UCA1 gene is measured by RT-PCR.

[5] A vaccinia virus, into which a UCA1 gene has been expressibly introduced.

[6] The vaccinia virus according to the above [5], which allows the UCA1 gene to express in cancer cells and replicates in the cancer cells by regulation of UCA1.

[7] The vaccinia virus according to the above [5] or [6], which is an oncolytic vaccinia virus.

[8] The vaccinia virus according to any one of the above [5] to [7], which is an LC16 strain, an LC16mO strain, or an LC16m8 strain modified to allow the expression of a B5R gene.

[9] A pharmaceutical composition for cancer therapy, comprising the vaccinia virus according to any one of the above [5] to [8].
[10] A pharmaceutical composition kit for cancer therapy, comprising an expression vector into which a UCA1 gene has been expressibly introduced, in combination with a vaccinia virus.
[11] The pharmaceutical composition kit for cancer therapy according to the above [10], wherein the vaccinia virus is an oncolytic vaccinia virus.
[12] The pharmaceutical composition kit for cancer therapy according to the above [10] or [11], wherein the vaccinia virus is an LC16 strain, an LC16mO strain, or an LC16m8 strain modified to allow the expression of a B5R gene.

The present description includes part or all of the contents as disclosed in the description and/or drawings of Japanese Patent Application No. 2015-145153, which is a priority document of the present application.

Advantageous Effects of Invention

The UCA1 gene acts as a host regulatory factor that enhances replication and/or propagation of a vaccinia virus in cancer cells. That is to say, when the expression level of the UCA1 gene is high in cancer cells, replication and/or propagation of the vaccinia virus in the cancer cells are enhanced. Accordingly, by using the expression level of the UCA1 gene in cancer cells collected from a cancer patient, the cancer virotherapeutic effects of the vaccinia virus on the cancer patient can be predicted and evaluated.

Moreover, by allowing the UCA1 gene to artificially express in the cancer cells or cancer tissues of the cancer patient, the cancer virotherapeutic effects of the vaccinia virus can be promoted.

BRIEF DESCRIPTION OF DRAWINGS

FIG. 1 shows a change in the drug resistance of KFtx (PTx resistant KF cells).
FIG. 2(a) shows the structure of a vaccinia virus,
and FIG. 2(b) shows the anticancer drug resistance of KFtx, LowTx, and Low.
FIG. 7-1 shows infection and/or replication of the vaccinia virus in the KFtx series, and this figure includes the observation images of the cells of the KFtx series.
FIG. 7-2 shows infection and/or replication of the vaccinia virus in the KFtx series, and shows virus titers.
FIG. 11-1 shows the results of the comparison of various ovarian cancer cell lines with one another, in terms of the replication and/or propagation ability of the vaccinia virus, and shows the observation images of the cells.
FIG. 11-2 shows the results of the comparison of various ovarian cancer cell lines with one another, in terms of the replication and/or propagation ability of the vaccinia virus, and shows virus titers.
FIG. 12-1 shows the infection images of the vaccinia virus in the KFtx series.
FIG. 12-2 shows the results of the quantification of the virus GFP fluorescence in the KFtx series.
FIG. 16-1 shows the virus infection images of the virus in the KFtx series, to which EGF stimulation has been given.
FIG. 16-2 shows the results of the quantification of GFP fluorescence in the KFtx series, to which EGF stimulation has been given.
In FIG. 16(a), quantification has been carried out under conditions of 10% FBS, whereas in FIG. 16(b), quantification has been carried out under conditions of 0.5% FBS.
FIG. 18-1 shows the virus infection images of the virus in various ovarian cancers.
FIG. 18-2 shows the results of the quantification of the virus GFP fluorescence in various ovarian cancers.
In FIG. 18-2(a), quantification has been carried out under conditions of MOI=0.01, whereas in FIG. 18-2(b), quantification has been carried out under conditions of MOI=0.001.
FIG. 19-1 shows the infection images of the virus of various ovarian cancers.
FIG. 19-2 shows the results of the quantification of the virus GFP fluorescence in various ovarian cancers.

DESCRIPTION OF EMBODIMENTS

Figure 3:
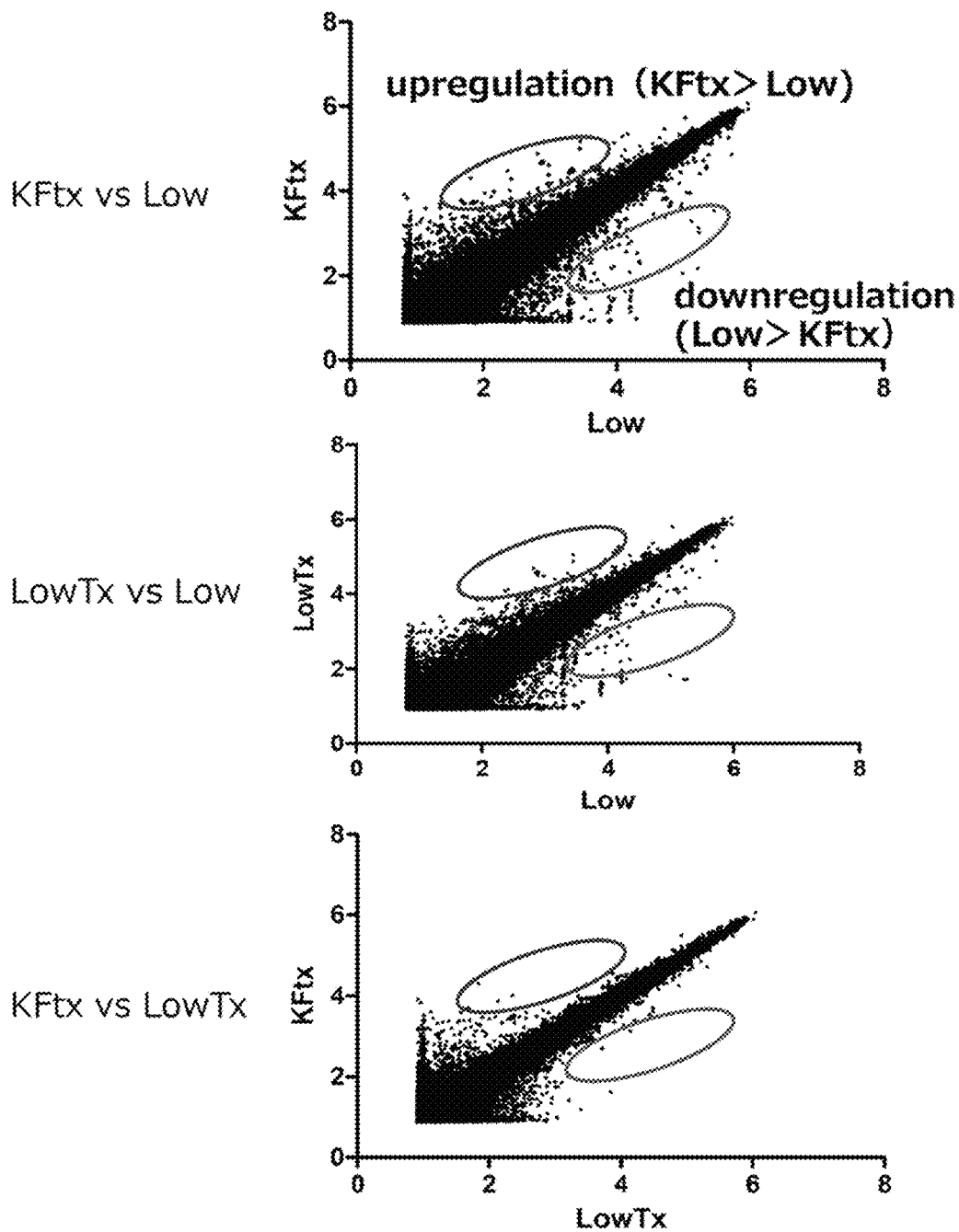
FIG. 3 shows the results of the comprehensive analysis of gene expression using a microarray, which has been carried out among KFtx, Low, and LowTx.

Hereinafter, the present invention will be described in detail.

UCA1 (Urothelial cancer associated 1) gene is a long-non coding RNA (lncRNA) gene that does not encode a protein.

The UCA1 gene has many variants. As examples of the nucleotide sequence of the UCA1 gene, a 2314-bp sequence (GenBank Accession No.: NR_015379.3) is shown in SEQ ID NO: 1, and a 1409-bp sequence (GenBank Accession No.: HQ833208.1) is shown in SEQ ID NO: 2.

In the present invention, UCA1 is utilized as a host regulatory factor that enhances replication and/or propagation of a vaccinia virus.

Specifically, when such a vaccinia virus is used in cancer virotherapy, a test is carried out to evaluate and predict whether or not the vaccinia virus has effects on cancer, using, as an indicator, the expression of the UCA1 gene in the cancer cells of a patient, and thereafter, auxiliary data for such evaluation and prediction is obtained. Such evaluation and prediction are also referred to as determination.

Moreover, when cancer virotherapy is carried out using the vaccinia virus, the UCA1 gene is allowed to express in cancer cells, so that the cancer therapeutic effects of the vaccinia virus can be promoted.

When lncRNA UCA1 that is a transcriptional product of the UCA1 gene is present in cancer cells, the lncRNA UCA1 enhances replication and/or propagation of the vaccinia virus in cancer cells. Conventionally, it has been reported that activation of ERK (Extracellular signal-regulated kinase) enhances the replication ability of the vaccinia virus. However, lncRNA UCA1 enhances the replication ability of the vaccinia virus, not through a pathway mediated by ERK, but through another pathway.

The strain of the vaccinia virus of the present invention is not limited. Examples of the strain include a Lister strain; an LC16 strain, an LC16mO strain, and an LC16m8 strain, which have been established from the Lister strain (Takashi Hashizume, *Rinsho to Virus* (Clinics and Viruses), Vol. 3, No. 3, 269, 1975, etc.); strains such as an NYBH strain; a Wyeth strain; and a Copenhagen strain. The LC16mO strain has been produced from the Lister strain, mediated by the LC16 strain, and the LC16m8 strain has been further produced from the LC16mO strain (*Tanpakushitsu, Kakusan, Koso* (Proteins, Nucleic Acids and Enzymes), Vol. 48, No. 12 (2003), pp. 1693-1700).

Preferably, the vaccinia virus is an oncolytic vaccinia virus (oncolytic virus) that is a vaccinia virus replicating only in cancer cells. The oncolytic vaccinia virus does not act on normal cells, but it replicates only in cancer cells, dissolves the cancer cells, and can effectively kill the cancer cells. The oncolytic vaccinia virus is also referred to as a limited replication type vaccinia virus.

From the viewpoint of establishing the safety of a vaccinia virus when it is administered to a human, the vaccinia virus used in the present invention is preferably attenuated and does not have pathogenicity. An example of such an attenuated strain is a strain comprising a partial or complete deletion of a B5R gene. The B5R gene encodes a protein existing in the envelope of the vaccinia virus, and the B5R gene product is associated with infection and/or replication of the virus. The B5R gene product is present in the surface of an infected cell and the envelope of the virus, and it acts to enhance infection efficiency, when the virus is infectious to and/or propagates to adjacent cells, or to other sites in the body of a host. The B5R gene product is also associated with the plaque size of the virus and the host range. If the B5R gene is deleted, the plaque size is decreased when animal cells are infected with the virus, and the pock size is also decreased. Moreover, the replication ability of the virus on the skin is decreased, and skin pathogenicity is decreased. In the vaccinia virus from which the B5R gene is partially or completely deleted, the gene product of the B5R gene does not have the normal function thereof, has low skin replication ability, and thus, even in a case it is administered to a human, it does not cause side effects. An example of such an attenuated strain comprising a deletion of the B5R gene is an m8Δ strain (which is also referred to as an LC16m8Δ strain) established by completely deleting the B5R gene from the above-described LC16m8 strain. In addition, an mOΔ strain (which is also referred to as an LCmOΔ strain) established by completely deleting the B5R gene from the LC16mO strain can also be used. These attenuated vaccinia virus strains obtained by partially or completely deleting the B5R gene are described in International Publication WO 2005/054451, and these attenuated strains can be acquired based on the description thereof. Whether or not the B5R gene has been partially or completely deleted from a vaccinia virus and the function of a B5R protein has been deleted, can be determined, for example, by using, as an indicator, the size of a plaque formed by infection of RK13 cells with the vaccinia virus, the pock size, the replication ability of the virus in Vero cells, skin pathogenicity in rabbits, etc. Alternatively, it may also be possible to examine the gene sequence of the vaccinia virus.

The vaccinia virus used in the present invention expresses the B5R gene in cancer cells, and gives damage to the cancer cells by action of the B5R protein. Accordingly, the vaccinia virus used in the present invention desirably expresses a complete B5R gene in cancer cells. In the case of using a vaccinia virus, which does not have a B5R gene as described above and has been attenuated, and the safety of which has been established, a complete B5R gene is introduced again into the vaccinia virus comprising a deletion of the B5R gene. In the case of using a vaccinia virus from which the B5R gene is partially or completely deleted, such a B5R gene may be inserted into the genome of the vaccinia virus, and may be then used. Insertion of the B5R gene into the vaccinia virus may be carried out by any method, and for example, a known homologous recombination method can be applied. In this case, the position, into which the B5R gene is to be inserted, may be a position located between a B4R gene and a B6R gene, in which the B5R gene has been originally present, or may also be any position on the genome of the vaccinia virus. Alternatively, a B5R gene has been previously constructed as a DNA construct, and it may be then introduced into the vaccinia virus.

Homologous recombination is a phenomenon by which two DNA molecules are recombined with each other in a cell, mediated by the same nucleotide sequence, and thus, the homologous recombination is a method frequently used in recombination of a virus having enormous genomic DNA, such as a vaccinia virus. First, a B5R gene is ligated to a vaccinia virus in such a manner that the sequence of a vaccinia virus gene site as a target is divided at the center, so as to construct a plasmid (which is referred to as a transfer vector), and this plasmid is introduced into cells that have been infected with the vaccinia virus. As a result, a recombination takes place between naked virus DNA that has become naked in the process of virus replication and the same sequence portion on the transfer vector, and the sandwiched B5R gene is incorporated into the virus genome. Examples of the cells that can be used herein include cells that can be infected with the vaccinia virus, such as BSC-1 cells, HTK-143 cells, Hep2 cells, MDCK cells, Vero cells, HeLa cells, CV1 cells, COS cells, RK13 cells, BHK-21 cells, and primary rabbit kidney cells. Moreover, introduction of the vector into the cells may be carried out by a known method such as a calcium phosphate method, a cationic liposome method, or an electroporation method.

Furthermore, a vaccinia virus that has been genetically modified to be used in cancer virotherapy can also be used. Examples of such a genetically modified vaccinia virus include the vaccinia virus described in International Publication WO 2011/125469 that is a vaccinia virus comprising the target sequence of micro RNA, the expression of which is reduced in cancer cells, and the vaccinia virus described in International Publication WO 2015/076422 that is a vaccinia virus, in which the functions of a vaccinia virus growth factor (VGF) and O1L are deleted.

The measurement of the expression of a UCA1 gene is carried out by measuring lncRNA UCA1 in a sample. Such measurement can be carried out using nucleotides comprising all or a part of the nucleotide sequence of the UCA1 gene as probes or primers. The measurement can be carried out by a quantitative PCR method of using, as a target, lncRNA UCA1 or a fragment thereof, or UCA1 cDNA or a fragment thereof. The measurement can also be carried out by a method of using a microarray (a microchip), a Northern blot method, etc. The measurement may be preferably carried out by a quantitative PCR method.

Examples of the quantitative PCR (Q-PCR) method include a quantitative RT-PCR method, a real-time PCR method, a Taqman (registered trademark) probe method, an SYBR Green method, an agarose gel electrophoresis method, a fluorescence probe method, an ATAC-PCR method (Kato, K. et al., Nucl. Acids Res., 25, 4694-4696, 1997), a Body Map method (Gene, 174, 151-158 (1996)), a Serial analysis of gene expression (SAGE) method (U.S. Pat. Nos. 527,154 and 544,861, and European Patent Application No. 0761822), and an MAGE method (Micro-analysis of Gene Expression) (JP Patent Publication (Kokai) No. 2000-232888 A). Among these methods, a TaqMan (registered trademark) probe method is preferable.

The PCR method can be carried out by a known means. The length (in bases) of the used primer is 5 to 50, preferably 10 to 30, and more preferably 15 to 25. A forward primer and a reverse primer may be designed based on the nucleotide sequence of the UCA1 gene, and may be then used.

The microarray can be produced by immobilizing nucleotides consisting of the nucleotide sequence of the UCA1 gene or nucleotides comprising a part of the sequence on a suitable substrate.

Examples of the immobilization substrate include a glass plate, a quartz plate, and a silicon wafer. Nucleotides or a fragment thereof can be immobilized on the immobilization substrate by a method of electrostatically binding the nucleotides with a solid-phased carrier, the surface of which has been treated with poly-cations such as polylysine, polyethyleneimine or polyalkylamine, utilizing the electric charge of the nucleotides, or a method of allowing nucleotides, into which a functional group such as an amino group, an aldehyde group, an SH group or biotin has been introduced, to bind to an immobilization substrate, into which a functional group such as an amino group, an aldehyde group or an epoxy group has been introduced, via a covalent bond, or other methods. Immobilization may be carried out using an array machine or a spotter. lncRNA UCA1, cDNA or a fragment thereof is solid-phased on a substrate to produce a microarray, the microarray is then allowed to come into contact with RNA or cDNA derived from the cancer cells of a cancer patient, which has been labeled with a fluorescent substance, carry out hybridization, and fluorescence intensity on the microarray is then measured, so that the expression of the UCA1 gene can be measured. The fluorescent substance used to label the RNA derived from the cancer cells is not limited, and a commercially available fluorescent substance can be used. Examples of such a fluorescent substance include Cy3 and Cy5. In the case of the method using a microarray, the fluorescence intensity can be measured using a nucleotide probe that hybridizes with lncRNA UCA1. The length (in bases) of the probe used in the measurement is 10 to 50 bp, and preferably 15 to 25 bp.

When the UCA1 gene is expressed in the cancer cells of a cancer patient, it can be determined that a vaccinia virus can be effectively utilized in cancer therapy for the patient. In addition, based on the expression level of the UCA1 gene, the degree of the effect of the vaccinia virus can be predicted and evaluated.

The expression level of the UCA1 gene is high in cancer cells having high anticancer drug resistance properties, and replication of the vaccinia virus is enhanced. Accordingly, the use of the vaccinia virus is effective, in particular, for patients to whom anticancer drugs have been continuously administered, and the cancer cells of whom are likely to acquire anticancer drug resistance.

The expression level of the UCA1 gene in cancer cells collected from a plurality of cancer patients has previously been measured, and based on the measurement value, a cut-off value (threshold) of the expression level of the UCA1 gene has been determined. Thereafter, the expression level of the UCA1 gene in cancer cells collected from a cancer patient, the effects of a vaccinia virus on which are to be evaluated, is measured. When the measured expression level exceeds the cut-off value, it can be evaluated that the vaccinia virus can be used in cancer virotherapy for the cancer patient.

Moreover, when the expression of the UCA1 gene is detected, it can also be evaluated that the vaccinia virus has cancer virotherapeutic effects on the cancer patient, and thus that the vaccinia virus can be used in cancer virotherapy for the cancer patient.

The present invention includes an invention relating to the use of the UCA1 gene for promoting the cancer therapeutic effects of a vaccinia virus on cancer cells, when cancer virotherapy is carried out using the vaccinia virus.

It has been reported that the UCA1 gene is associated with the anticancer drug resistance properties of cancer cells. lncRNA UCA1 enhances the replication ability of the vaccinia virus in cancer cells having high resistance properties to anticancer drugs, for example, to Paclitaxel (PTx).

A cancer patient may be treated using a vaccinia virus in a state in which lncRNA UCA1 is allowed to exist in the cancer cells of the patient who is to be subjected to cancer therapy. lncRNA UCA1 may have previously been administered to cancer cells, or a UCA1 gene may be administered to cancer cells, and lncRNA UCA1 may be then allowed to express in the cancer cells.

The expression of the UCA1 gene in cancer cells can be carried out using an expression vector comprising a UCA1 gene. Specifically, such an expression vector comprising a UCA1 gene may be expressibly introduced into the cancer cells of a cancer patient, and the UCA1 gene may be then allowed to express in the cancer cells.

In order to allow a UCA1 gene to express in cancer cells, the UCA1 gene needs to be introduced into the cancer lesion of a patient. Introduction of the gene can be carried out according to a known method. As a method of introducing a gene into a cancer patient, a method of using a viral vector or a method of using a non-viral vector such as a plasmid can be applied. These methods are described in *Bessatsu Jikken Igaku* (Separate Volume of Experimental Medicine), *Idenshi Chiryo no Kiso Gijyutsu* (Basic Technology of Gene Therapy), Yodosha Co., Ltd., 1996; *Bessatsu Jikken Igaku* (Separate Volume of Experimental Medicine), *Idenshi Donyu & Hatsugen Kaiseki Jikken Ho* (Gene Introduction & Expression Analysis Experimental Method), Yodosha Co., Ltd., 1997; *Idenshi Chiryo Kaihatsu Kenkyu Handbook* (Gene Therapy Development Research Handbook), edited by Japan Society of Gene Therapy, N T S, 1999; Walter J. Burdette, *Shitteokitai Idenshi Chiryo no Kiso Chishiki* (Basic Knowledge of Gene Therapy to be Known), Takara Bio, 2004; etc.

Examples of the viral vector used for introduction of the UCA1 gene include viral vectors such as adenovirus, adeno-associated virus (AAV), retrovirus, lentivirus, vaccinia virus, and Sendai virus. A desired gene is introduced into DNA virus or RNA virus, such as detoxified retrovirus, herpes virus, poxvirus, poliovirus, Sindbis virus, Sendai virus, SV40, or human immunodeficiency virus (HIV), and thereafter, cells are infected with the recombinant virus, so that the UCA1 gene can be introduced into the cells.

The viral vector, into which the UCA1 gene has been introduced, becomes infectious to cells, mediated by a specific receptor.

Moreover, although the above-described virus is not used, the UCA1 gene can be introduced into target cells or tissues by using a recombinant expression vector into which a gene expression vector has been incorporated, such as a plasmid. The UCA1 gene can be introduced into cells by applying methods such as a phosphoric acid-calcium co-precipitation method, a lipofection method, a DEAE-dextran method, or a method of directly injecting DNA using a micro glass tube. Furthermore, the recombinant expression vector can be introduced into target cells or tissues by applying: methods of using a liposome, such as a gene introduction method of using an internal liposome, a gene introduction method of using an electrostatic type liposome, an HVJ-liposome method, or a modified HVJ-liposome method (HVJ-AVE liposome method); a method of using an HVJ-E (envelope) vector; a receptor-mediated gene introduction method; a naked DNA direct introduction method; a method of introducing DNA together with gold particles, using a particle gun; introduction methods using various polymers; etc. For this purpose, any expression vector can be used, as long as it is a vector capable of expressing a UCA1 gene in a living body. Examples of the expression vector that can be used herein include pCMV6, pBK-CMV, pcDNA3.1, pZeoSV (Invitrogen, Stratagene), pCAGGS (Gene 108, 193-200 (1991)), and pVAXI.

The expression vector comprising the UCA1 gene may also comprise a promoter, an enhancer, a poly A signal, a marker gene, and the like. As a promoter, a known promoter can be used.

In the above-described method, before cancer therapy is carried out using a vaccinia virus, lncRNA UCA1 has previously been expressed in the cancer cells of a cancer patient. Alternatively, a UCA1 gene is introduced into a vaccinia virus to be used in cancer therapy, so that the vaccinia virus itself for use in the cancer therapy is allowed to express the UCA1 gene, and thereafter, the vaccinia virus may be administered to a cancer patient. In this case, the cancer cells are infected with the vaccinia virus and lncRNA UCA1 is then expressed in the cancer cells, so that the vaccinia virus replicates in the cancer cells by regulation of the UCA1 gene, and the cancer virotherapeutic effects of the vaccinia virus are enhanced.

The present invention includes a vaccinia virus into which a UCA1 gene is expressibly incorporated and introduced, and a pharmaceutical composition for cancer therapy, comprising the aforementioned vaccinia virus. In addition, the present invention also includes a pharmaceutical composition kit for cancer therapy, comprising an expression vector into which a UCA1 gene has been expressibly incorporated and introduced, in combination with a vaccinia virus.

The cancer as a target of the cancer virotherapy using a vaccinia virus is not limited. Examples of the cancer include all types of cancers, such as ovarian cancer, lung cancer, pancreatic cancer, skin cancer, stomach cancer, liver cancer, colon cancer, anal-rectal cancer, esophageal cancer, uterine cancer, breast cancer, bladder cancer, prostate cancer, brain and nervous tumor, lymphoma, leukemia, bone and bone sarcoma, leiomyoma, and rhabdomyoma.

The pharmaceutical composition for cancer therapy comprising the vaccinia virus of the present invention can be formulated into the form of an aseptic aqueous or non-aqueous solution, suspension, or emulsion, which comprises, as an active ingredient, a pharmaceutically effective amount of vaccinia virus. Moreover, the pharmaceutical composition for cancer therapy of the present invention may further comprise a pharmaceutically acceptable diluent, auxiliary agent, carrier, etc., such as salts, a buffer or an adjuvant. The pharmaceutical composition may be administered to a cancer patient via a parenteral administration route, such as a subcutaneous, intravenous, intradermal, intramuscular, intraperitoneal, intranasal, or transdermal route. Furthermore, the pharmaceutical composition may also be locally administered to a cancerous portion. The effective dose can be determined, as appropriate, depending on the age, sex, health condition, body weight, etc. of a cancer patient. For example, in the case of a human adult, approximately $10^2$ to $10^{10}$ plaque forming units (PFU) per dose, and preferably $10^5$ to $10^6$ plaque forming units (PFU) per dose may be administered to the subject.

EXAMPLES

The present invention will be specifically described in the following examples. However, these examples are not intended to limit the scope of the present invention.

Example 1

Relationship Between Paclitaxel Resistance and Vaccinia Replication in KF (Ovarian Cancer)

Figures 1, 11:
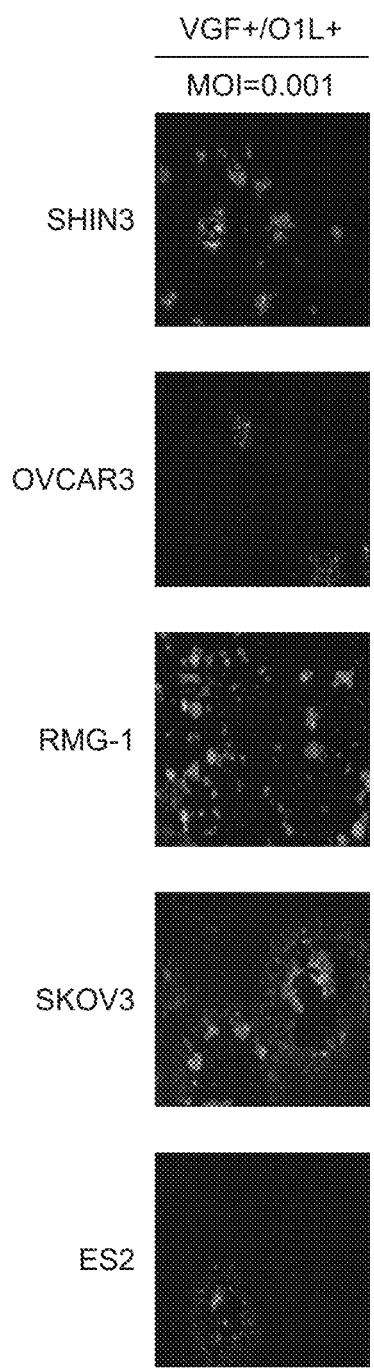
Figures 2, 11:
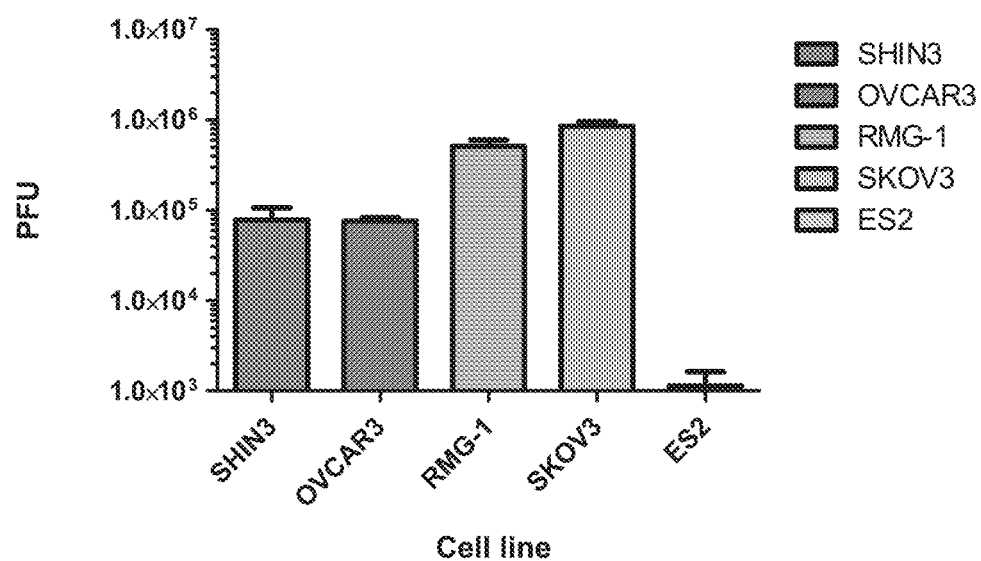

When KFtx (PTx-resistant KF) was continuously cultured in a 10% FBS-containing RPMI medium that did not contain the anticancer drug PTx (Paclitaxel), the PTx resistance properties of the KFtx were reduced. Such a strain with decreased PTx resistance properties was defined as Low. Subsequently, when Low was cultured in 62.5 nM PTx in RPMI medium, the PTx resistance properties of Low were recovered. Such a strain with recovered PTx resistance properties was defined as LowTx (FIG. 1). When LowTx was cultured without PTx, the resistance properties of LowTx were reduced. Accordingly, the resistance properties can be said to be reversible.

Thereafter, genes encoding O1L and VGF, which are active factors for the Ras/Raf/MEK/ERK metabolic pathway of the vaccinia virus LC16mO strain, were replaced with luciferase, GFP or DsRed, so as to produce deleted virus strains. In an O1L+/VGF+ virus, an HA gene, which is not an active factor for the Ras/Raf/MEK/ERK metabolic pathway, was replaced with luciferase or GFP, so that this gene was deleted (FIG. 2(a)). Subsequently, the KFtx series were seeded on a 96-well plate, and 36 hours later, the cells were infected with VGF+/O1L+ at MOI=0.01. Seventy-two hours after the infection, GFP fluorescence in the resulting cells was photographed using a fluorescence microscope (Olympus) (FIG. 2(b)). As a result, virus replication was increased in cells having high anticancer drug resistance properties. Accordingly, it was suggested that Paclitaxel resistance properties and virus replication have a positive correlation.

Example 2

Extraction of Candidate Gene UCA1 and Production of Cell Line Stably Expressing UCA1

Figure 4:
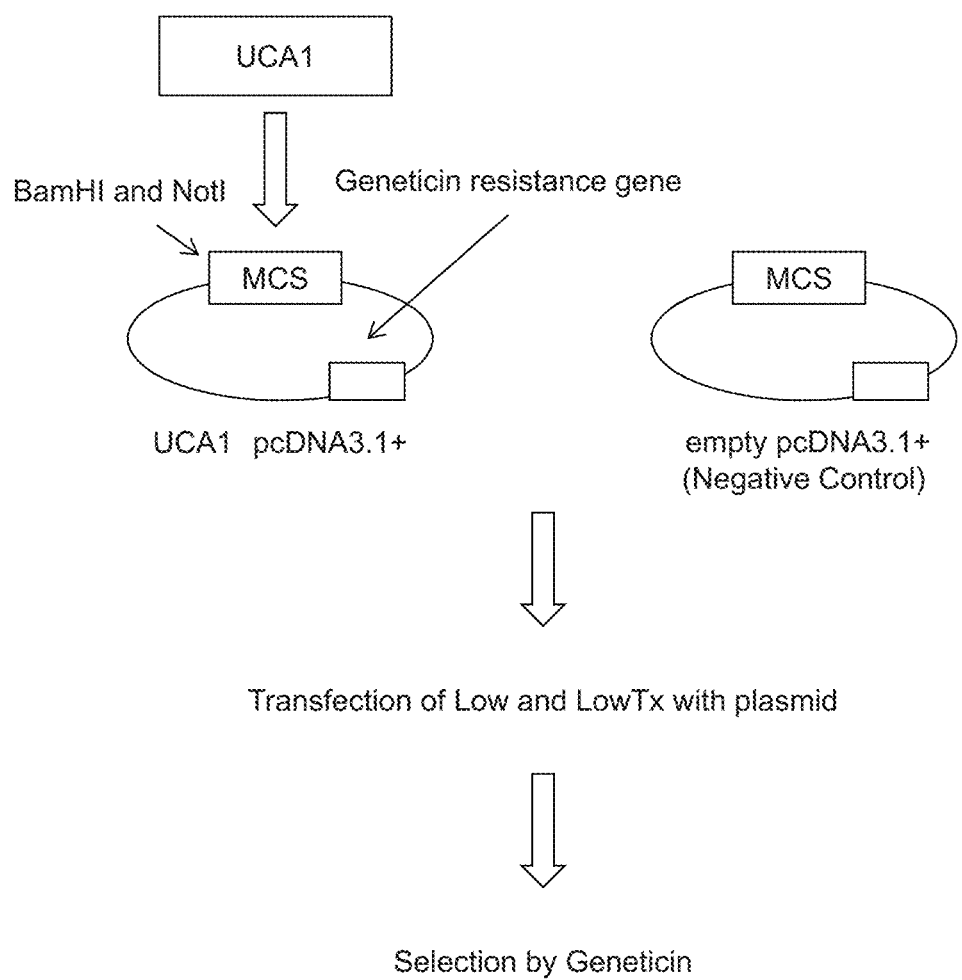
FIG. 4 shows a method of transfection of the UCA1 gene.
Figure 5:
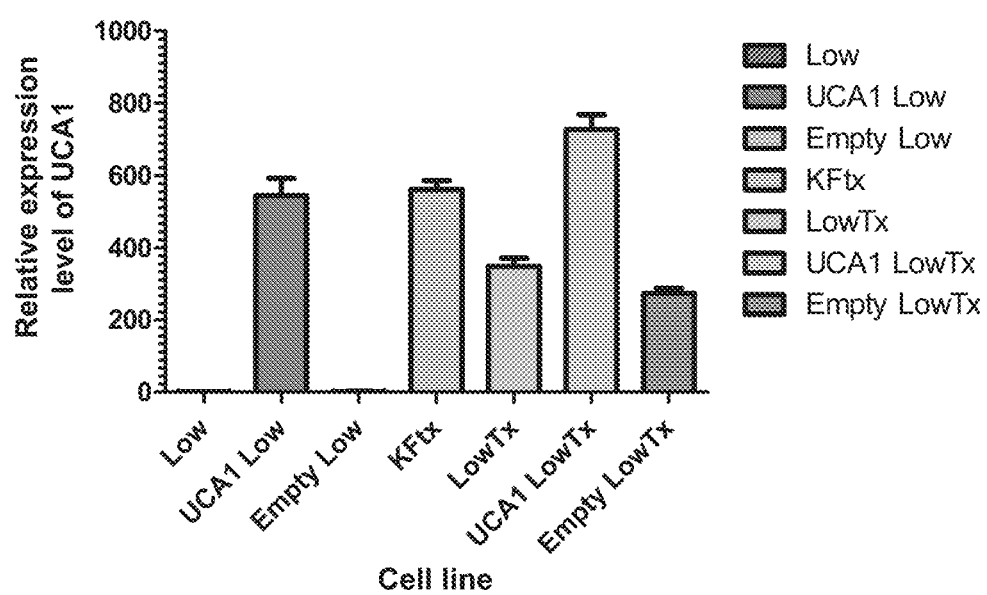
FIG. 5 shows the results of the confirmation of enhanced expression of UCA1 by qRT-PCR.

Three types of strains KFtx, Low, and LowTx were subjected to a comprehensive gene expression analysis using a microarray (Takara Bio Inc.). A gene, the expression of which was promoted in a cell line having high virus replication and high anticancer drug resistance, and the expression of which was suppressed in a cell line having low virus replication and low anticancer drug resistance, was extracted as a candidate gene. FIG. 3 shows the results of the comprehensive analysis of the gene expression using a microarray. FIG. 3 shows the results of the analysis of a gene, the expression of which was promoted or suppressed among KFtx. LowTx and Low. UCA1 extracted as a candidate gene is Long-non coding RNA, and UCA1 has also been identified as an oncogene in various other cancers such as ovarian cancer, bladder cancer and stomach cancer. In order to produce a cell line stably expressing this UCA1, RNA was extracted from KFtx, using NucleoSpinRNA (Takara Bio Inc.) according to the manual included therewith. RT-PCR (Reverse Transcription Polymerase Chain Reaction) was performed on this RNA, using High-Capacity cDNA Reverse Transcription Kit according to the manual included therewith, so that cDNA was produced from the RNA. The produced cDNA was used as a template, and a UCA1 gene, to both termini of which the restriction enzymes BamH1 and Not1 were added, was amplified using two primers 5'-ctggatcctgacattcttctggacaatgag-3' (SEQ ID NO: 4) and 5'-ctgcggccgcatattagctttaatglaggtggc-3' (SEQ ID NO: 5). The sequence of the UCA1 gene, to both termini of which the restriction enzymes BamH1 and Not1 were added, is shown in SEQ ID NO: 3. The sequence portion from t at position 7 to c at position 1414 in the sequence shown in SEQ ID NO: 3 is the sequence of the UCA1 gene, and this sequence corresponds to the nucleotides from position 1 to position 1408 in SEQ ID NO: 1. However, a at position 797 in SEQ ID NO: 1 is replaced with t. This PCR product was cleaved with BamH1 and Not1, and it was then cloned into the same restriction enzyme site of pcDNA3.1(+) to obtain pcDNA3.1 (+)-UCA1. Subsequently, Low and LowTx, which had been seeded on a 24-well plate, were transfected with pcDNA3.1 (+)-UCA1 and a negative control pcDNA3.1(+), using Fugene HD (Promega) and ProFection Mammalian Transfection System (Promega) (wherein calcium phosphate was used). LowTx transfected with the UCA1 gene through pcDNA3.1(+)-UCA1 was referred to as UCA1 LowTx, and Low transfected with the UCA1 gene through pcDNA3.1 (+)-UCA1 was referred to as UCA1 Low. In addition, LowTx transfected with pcDNA3.1(+) containing no UCA1 was referred to as Empty LowTx, and Low transfected with pcDNA3.1(+) containing no UCA1 was referred to as Empty Low. FugeneHD was used for UCA1 LowTx and Empty LowTx, whereas calcium phosphate was used for UCA1 Low and Low. Thereafter, selection was conducted using Geneticin, so as to obtain a cell line stably expressing UCA1. FIG. 4 shows a method of transfection with the UCA1 gene. In order to confirm the increased expression of UCA1, qRT-PCR was carried out on this cell line stably expressing UCA1. RNA was extracted from each cells using NucleoSpinRNA, and cDNA was then produced from the extracted RNA according to RT-PCR (Reverse Transcription PCR). Using TaqMan probe (Life Technologies, Assay ID: Hs01909129_s1), qRT-PCR was carried out (n=3). GAPDH (Life Technologies, Assay ID: Hs03929097_g1) was selected as a reference gene. The relative expression level of UCA1 was calculated according to a comparative Ct method, using GAPDH as a reference. The expression of UCA1 was confirmed in the cell line stably expressing UCA1, at a level equivalent to KFtx. On the other hand, it was confirmed that the expression of UCA1 was not enhanced in the cell line stably expressing pcDNA3.1(+) used as a negative control (FIG. 5).

Example 3

Properties of UCA1 in KFtx Series

Figure 6:
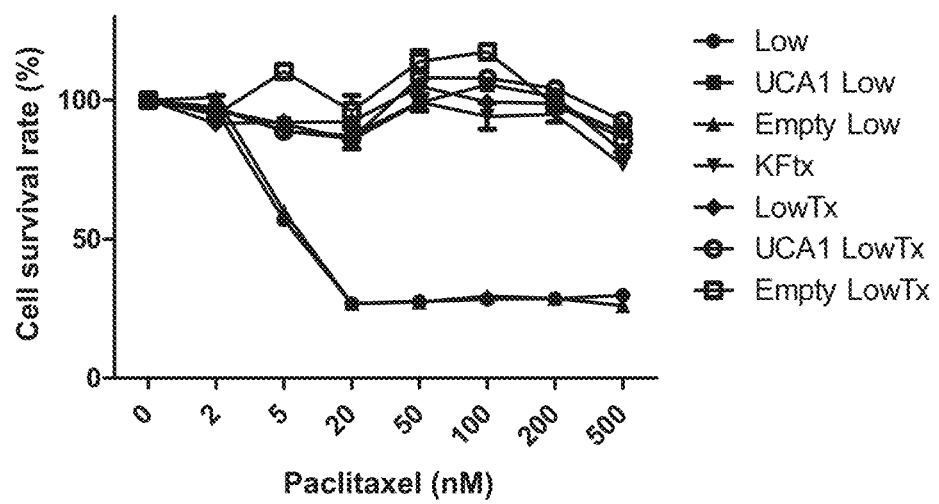
FIG. 6 shows the results of the comparison of the KFtx series in terms of PTx resistance properties.

Paclitaxel resistance properties of the KFtx series comprising the cell line stably expressing UCA1 were compared. The KFtx series were seeded at a cell density of $6 \times 10^3$/well on a 96-well plate, and after the cells had been cultured at 37° C. for 12 hours, during which the cells were considered to adhere to the plate, the medium was exchanged with PTx-containing RPMI. The concentrations of PTx were set to be 0, 2, 5, 20, 50, 100, 200, and 500 nM. The cells were further cultured at 37° C. for 48 hours, and the number of surviving cells was then quantified using Cell Titer-Glo (Promega) and was then compared. As a result, it was found that the number of surviving cells was significantly decreased in Low and Empty Low, in which the expression of UCA1 was low (FIG. 6). From these results, it was considered that high expression of UCA1 would be important for Paclitaxel resistance properties.

Figures 2, 7:
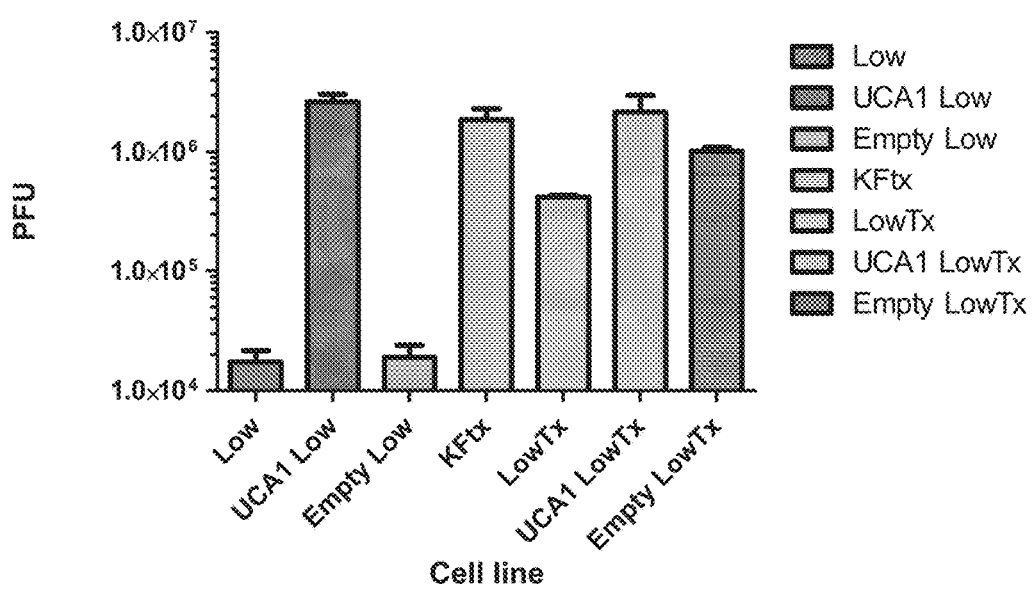

Subsequently, high expression of UCA1 and the replication ability of the vaccinia virus in the KFtx series were compared. The KFtx series were seeded at a cell density of $6 \times 10^3$/well on a 96-well plate, and after the cells had been cultured at 37° C. for 36 hours, the cultured cells were infected with VGF+/O1L+ and with VGF-/O1L- at MOI=0.01 and 0.001, respectively. The cells were further cultured at 37° C. for 72 hours. Thereafter, living cells were directly subjected to bright field observation and fluorescence observation, using a fluorescence microscope (FIG. 7-1). As a result, the degree of MOI reflected on the intensity of GFP fluorescence in both types of viruses. Cells emitting green fluorescence as a result of infection with VGF+/O1L+ comprised a large amount of KFtx and a small amount of Low. In addition, the cells emitting green fluorescence comprised LowTx in an amount intermediate of the KFtx and the Low. Low and Empty Low as a control thereof, and also, LowTx and Empty LowTx as a control thereof, were comprised in almost the same amounts, and there was no great difference in the number of cells emitting green fluorescence. In contrast, it was observed that UCA1 Low and UCA1 LowTx, which were cell lines stably expressing UCA1, comprised a large number of cells emitting green fluorescence. A difference among cells infected with VGF-/O1L- was similar to the difference among cells infected with VGF+/O1L+. When compared with Low, LowTx, Empty Low, and Empty LowTx, a large number of cells emitting green fluorescence were observed in UCA1 Low and UCA1 LowTx, at the same level as in the case of KFtx. From these results, it became clear that the expression of UCA1 and the replication ability of the vaccinia virus show a positive correlation, regardless of the type of the vaccinia virus. Furthermore, in order to verify, in detail, the correlation of high expression of UCA1 with the replication ability of the vaccinia virus, titration was carried out. The KFtx series were seeded at a cell density of $6 \times 10^3$/well on a 96-well plate, and were then cultured at 37° C. for 36 hours. Thereafter, the cultured cells were infected with VGF+/O1L+ at MOI==0.001 (n=3). The resulting cells were further cultured at 37° C. for 72 hours, and each supernatant and infected cells were recovered, followed by freezing and thawing, and then, sonication. Then, the supernatant obtained after centrifugation (2,000 rpm, 5 minutes) was recovered as a virus solution. The virus titer of each virus solution (1 ml) was measured using RK13 cells (FIG. 7-2). As a result, it corresponded to the observation image obtained under a fluorescence microscope.

These results show that the replication and/or propagation ability of the virus is enhanced by transfection with UCA1, when compared with the control. Moreover, high expression of UCA1 enhanced the replication and/or propagation ability of the vaccinia virus. From these results, it was confirmed that high expression of UCA1 in the KFtx series enhances the replication ability of the vaccinia virus.

Example 4

Figure 8:
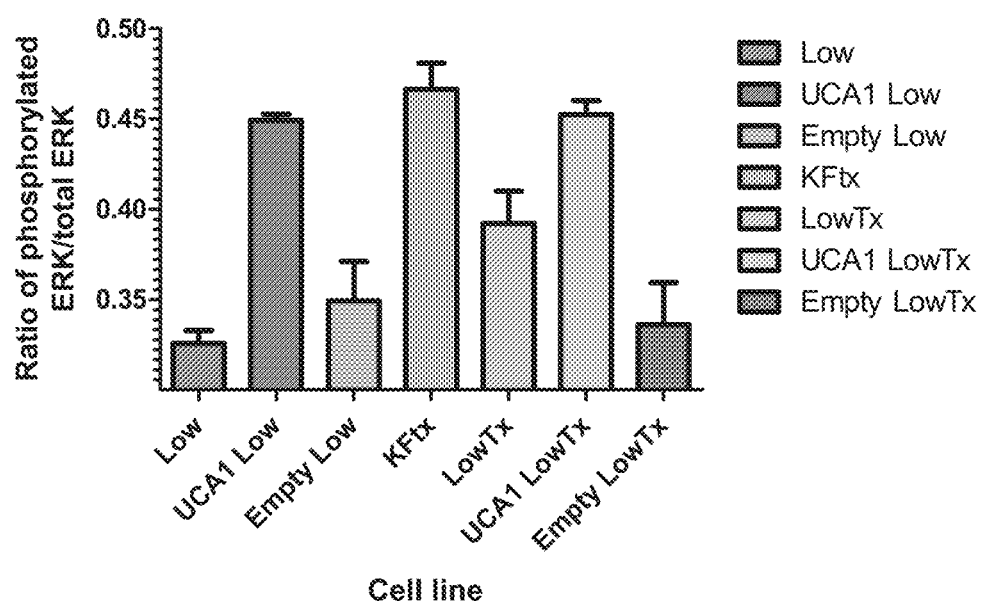
FIG. 8 shows the expression of activated ERK (phosphorylated ERK) in the KFtx series.

Relationship Between Replication Ability of Vaccinia Virus Regulated by High Expression of UCA1 and Activation of ERK The enhancement of the replication ability of the vaccinia virus by UCA1 was analyzed in detail. Since it has been reported that activation of ERK enhances the replication ability of the vaccinia virus, the relationship between activation of ERK and high expression of UCA1 was analyzed. The KFtx series were seeded at a cell density of $6\times10^3$/well on a 96-well plate, and were then cultured at 37° C. for 36 hours. Thereafter, using Pierce Colorimetric In-Cell ELISA Kits, total ERK and activated ERK (phosphorylated ERK) in the total ERK were measured (FIG. 8). As a result, the percentage of the phosphorylated ERK was low in Low and Empty Low, and as the expression of UCA1 increased, the percentage of the phosphorylated ERK also increased. That is to say, the percentage of the phosphorylated ERK fluctuated in proportion to the expression of UCA1. Since ERK is associated with the replication and/or propagation ability of the virus, it was suggested that UCA1 controls the activation of ERK, and thereby regulates the replication of the virus, namely, that high expression of UCA1 is not only associated with the replication ability of the vaccinia virus, but also with activation of ERK.

Figure 9:
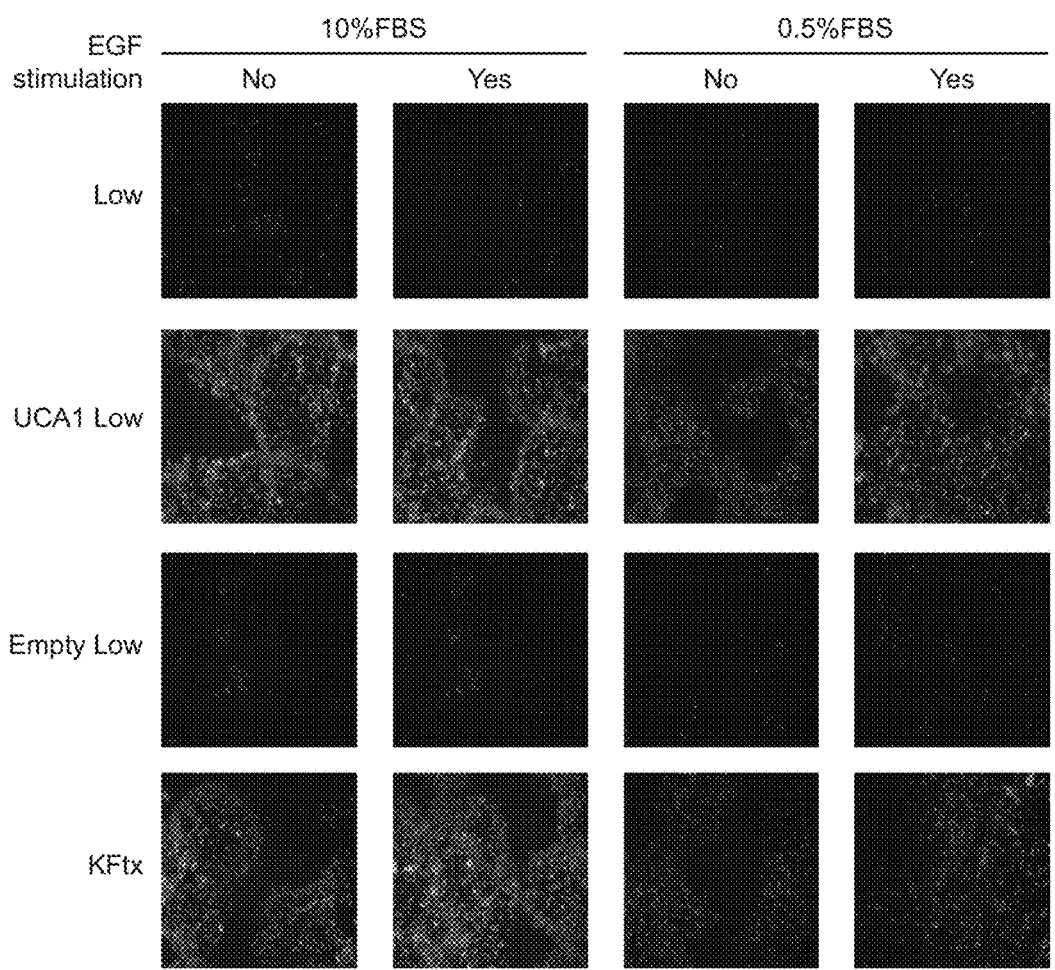
FIG. 9 shows a change in the replication of the vaccinia virus by EGF stimulation.

Subsequently, a change in the replication ability of the vaccinia virus caused by activation of ERK was measured. EGFR, a receptor of ERK, is present upstream of the ERK, and when EGF binds to EGFR, by way of an adapter molecule and a low molecular weight G protein Ras, signals are transmitted through a MARK pathway having a phosphorylation reaction with Raf→MEK→ERK. The activated ERK finally transfers to the nucleus, and a transcriptional factor is activated, so that genes associated with cell growth and cell differentiation are expressed. The KFtx series were seeded at a cell density of $6\times10^3$/well on a 96-well plate, and were then cultured at 37° C. for 12 hours (10% FBS RPMI). Thereafter, the medium was exchanged with RPMI containing 10% FBS or 0.5% FBS. The cultured cells were further cultured at 37° C. for 24 hours (36 hours after the seeding), and the resulting cells were then infected with VGF+/O1L+ at MOI=0.01. The thus infected cells were further cultured at 37° C. for 72 hours, and thereafter, living cells were directly subjected to bright field observation and fluorescence observation using a fluorescence microscope (FIG. 9). It is to be noted that some cells were stimulated with 0.2 ng/μl EGF 30 minutes before the infection. As a result, in 10% FBS, KFtx and UCA1 Low comprised a large number of cells emitting green fluorescence, whereas Low and Empty Low comprised a small number of cells emitting green fluorescence. Moreover, no change was observed due to the presence or absence of EGF stimulation. Also in 0.5 FBS, the same tendency as described above was found. That is, although the number of cells emitting green fluorescence in 0.5% FBS was entirely decreased in comparison to that in 10% FBS, KFtx and UCA1 Low comprised a large number of cells emitting green fluorescence, whereas Low and Empty Low comprised a small number of cells emitting green fluorescence. Moreover, no change was observed due to the presence or absence of EGF stimulation. As such, the replication ability of the vaccinia virus was not enhanced by EGF stimulation. From these results, it was found that the enhancement of the replication ability of the vaccinia virus was not confirmed in the KFtx series by activation of ERK. That is, it was considered that UCA1 enhances virus replication by regulating not only ERK alone, but also other pathways.

The results of Example 3 and Example 4 suggested that high expression of UCA1 acts on not ERK, but other pathways, so that it enhances the replication ability of the vaccinia virus.

Example 5

Significance of UCA1 in Various Ovarian Cancer Cell Lines

Figure 10:
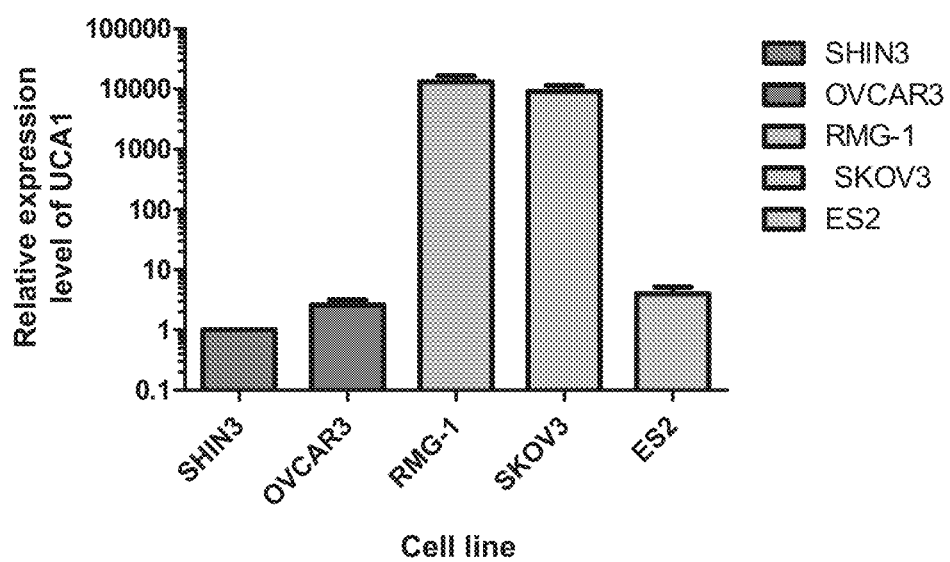
FIG. 10 shows a comparison of various ovarian cancer cell lines in terms of the expression of UCA1.

The phenomenon of the enhancement of the replication ability of the vaccinia virus by high expression of UCA1 was verified using cell lines other than the KFtx series. Five types of cell lines SHIN3, OVCAR3, RMG-1, SKOV3, and ES2 were seeded on a 6-well plate. The cells of each cell line were cultured at 37° C. for 36 hours, and RNA was then extracted and recovered from the cells of each cell line, using NucleoSpinRNA. Thereafter, cDNA was produced from the RNA according to RT-PCR. Using the cDNA as a template, the expression of UCA1 was quantified according to qRT-PCR employing TaqMan probe (Life Technologies, Assay ID: Hs01909129_s1) (n=3). GAPDH (Life Technologies, Assay ID: Hs03929097_g1) was used as a reference gene. The relative expression level of UCA1 was calculated according to a comparative Ct method, using GAPDH as a reference. As a result, differences in the expression of UCA1 were found among the cell lines (FIG. 10).

Subsequently, the 5 types of ovarian cancer cell lines were each seeded at a cell density of $1\times10^4$/well on a 96-well plate, and were then cultured at 37° C. for 36 hours. Thereafter, the cells of each cell line were infected with VGF+/O1L+ at MOI=0.001. The resulting cells were further cultured at 37° C. for 72 hours, and thereafter, living cells were directly subjected to bright field observation and fluorescence observation, using a fluorescence microscope (FIG. 11-1). As shown in FIG. 11-1, RMG-1 and SKOV3 comprised a large number of cells emitting green fluorescence. Specifically, it was suggested that high expression of UCA1 and the replication ability of the vaccinia virus have a positive correlation. Thereafter, the 5 types of ovarian cancer cell lines were seeded at a cell density of $1\times10^4$/well on a 96-well plate, and were then cultured at 37° C. for 36 hours. Thereafter, the cells of each cell line were infected with VGF+/O1L+ at MOI=0.001. The resulting cells were further cultured at 37° C. for 72 hours, and thereafter, each supernatant and infected cells were recovered, and were then subjected to titration using RK-13 (FIG. 11-2). As shown in FIG. 11-2, the replication and/or propagation ability of the virus was low in SHIN3, OVCAR3 and ES2, in which the expression of UCA1 was low, and on the other hand, the replication and/or propagation ability of the virus was high in RMG-1 and SKOV3, in which the expression of UCA1 was high. That is to say, the same results as those of the observation images were obtained. From these results, it was confirmed that high expression of UCA1 and the replication ability of the vaccinia virus have a positive correlation.

Furthermore, since this phenomenon was not only observed in KFtx, but the same results were also obtained in other ovarian cancers, it was suggested that this phenomenon was broadly preserved in ovarian cancers.

Example 6

Figures 1, 12:
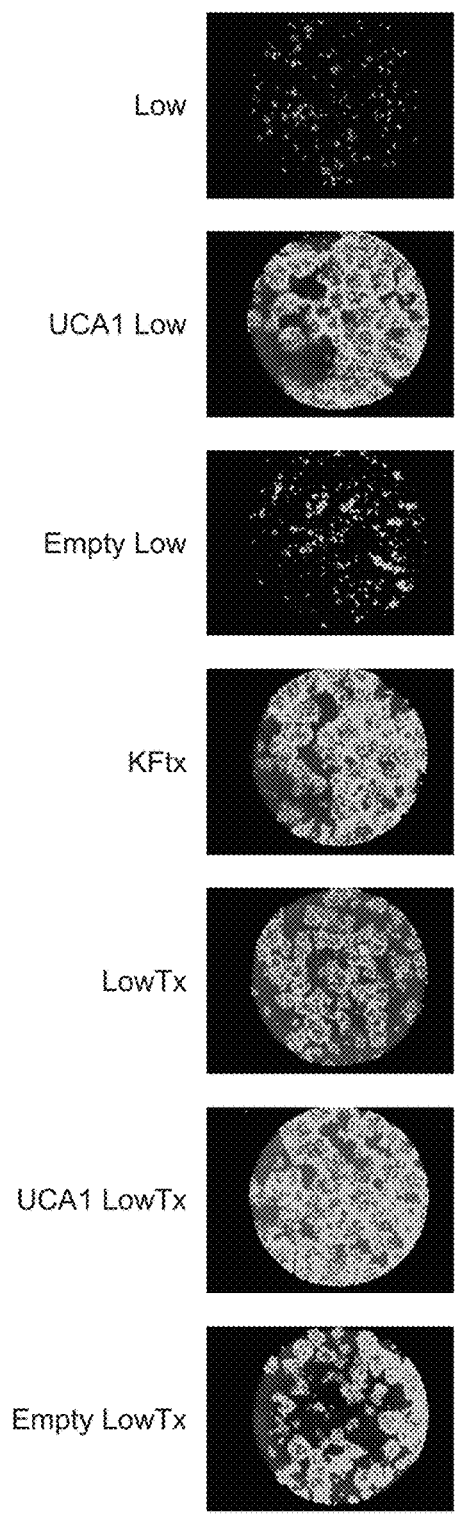
Figures 2, 12:
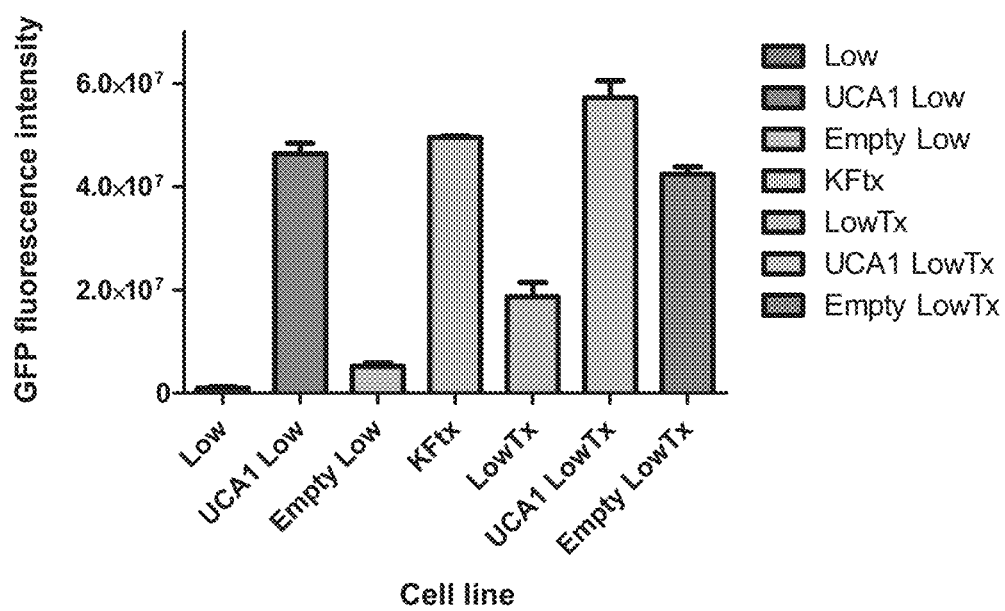

Studies Regarding the Relationship of Expression of UCA1, with the Replication Ability, Virus-producing Ability and Oncolytic Property of the Vaccinia Virus in KFtx Series (1) Virus Infected Images in KFtx Series and Quantification of Virus GFP Fluorescence The high expression of UCA1 and the replication ability of the vaccinia virus in the KFtx series were compared. The KFtx series (Low, UCA1 Low, Empty Low, KFtx. LowTx, UCA1 LowTx and Empty LowTx) were seeded at a cell density of $6\times10^3$/well on a 96-well plate, were then cultured at 37° C. for 36 hours, and were then infected with VGF+/O1L+ at MOI=0.01 (n=3). The resulting cells were cultured at 37° C., and 72 hours after the infection, using the Keyence fluorescence microscope BZ-X710, living cells were directly subjected to fluorescence observation, and at the same time, the fluorescence intensity was converted into a numerical value. The infected images are shown in FIG. 12-1, and the results of quantification of the fluorescence are shown in FIG. 12-2. As shown in FIG. 12-1, the fluorescence intensity was strong in UCA1 Low and UCA1 LowTx. and the expression level of UCA1 and the replication and propagation ability of the virus have a positive correlation. Moreover, as shown in FIG. 12-2, the fluorescence intensity of GFP corresponded to the observation images obtained under a fluorescence microscope.

(2) Time Lapse Infection and Replication Images of Viruses in KFtx Series

Figure 13:
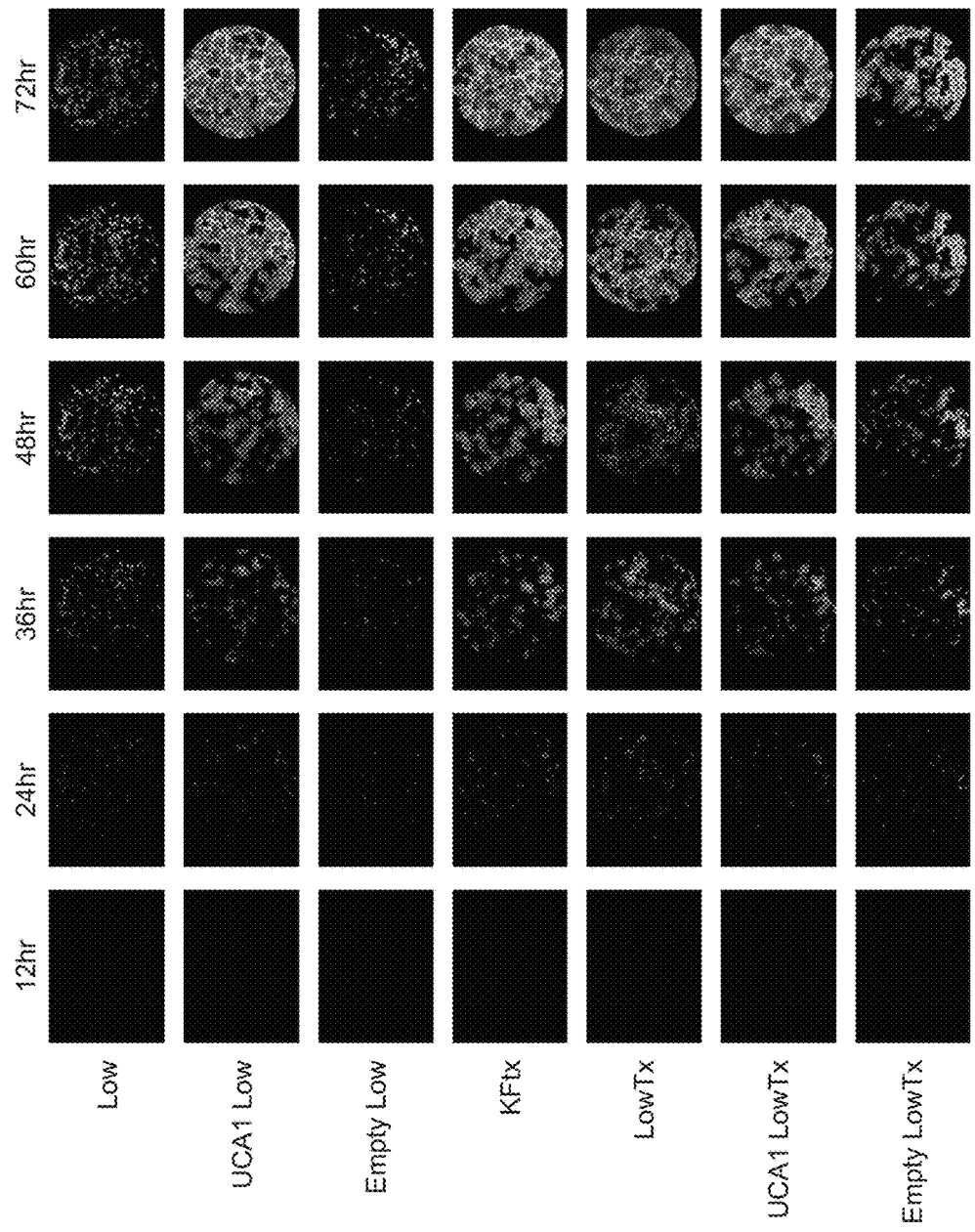
FIG. 13 shows the time-lapsed infection and replication images of the vaccinia virus in the KFtx series.

High expression of UCA1 and the replication ability of the vaccinia virus in the KFtx series were compared in a time lapse manner. The KFtx series (Low, UCA1 Low, Empty Low, KFtx, LowTx, UCA1 LowTx and Empty LowTx) were seeded at a cell density of $6\times10^3$/well on a 96-well plate, and were then cultured at 37° C. for 36 hours. Thereafter, the cultured cells were infected with VGF+/O1L+ at MOI=0.01 (n=3). The resulting cells were cultured at 37° C., and thereafter, from 12 to 72 hours after the infection, living cells were directly subjected to bright field observation and fluorescence observation, every 12 hours, using the Keyence fluorescence microscope BZ-X710. The infected images are shown in FIG. 13. As shown in FIG. 13, it was confirmed in a time lapse manner that the expression of UCA1 and the replication ability of the vaccinia virus have a positive correlation.

(3) Change in Expression of UCA1 Associated with Virus Infection of KFtx Series

Figure 14:
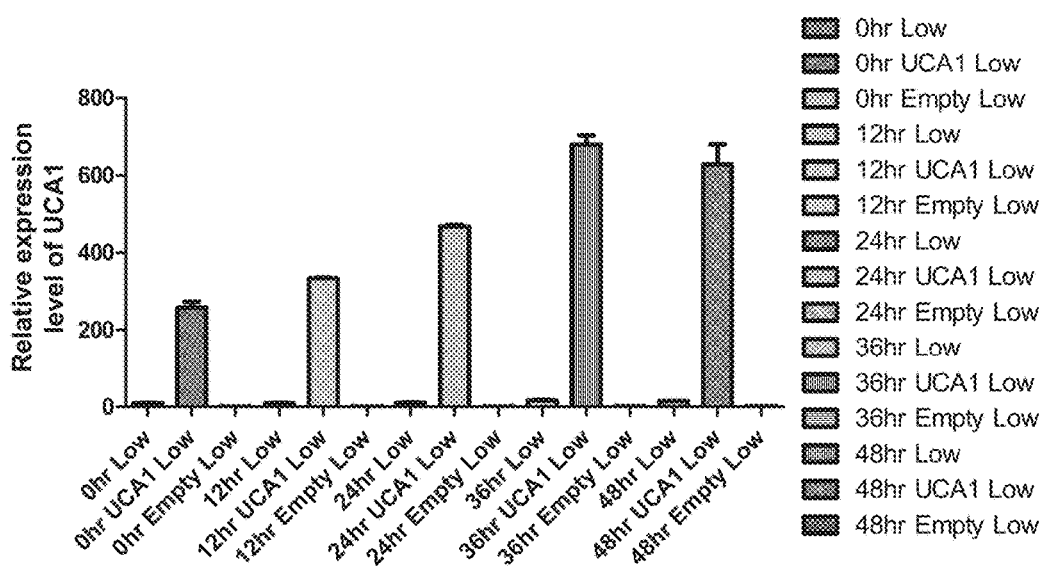
FIG. 14 shows a time-dependent change in the expression of UCA1 by infection of the vaccinia virus.

The expression level of UCA1 and the replication ability of the virus were compared in a time lapse manner. The KFtx series (Low, UCA1 Low, and Empty Low) were seeded at a cell density of $3\times10^4$/well on a 24-well plate, and were then cultured at 37° C. for 36 hours. Thereafter, the cultured cells were infected with VGF+/O1L+ at MOI=0.01. Immediately before the infection, and also, 12 hours, 24 hours, 36 hours and 48 hours after the infection, RNA was recovered, and cDNA was produced from the RNA according to RT-PCR. Such RNA was extracted and recovered using NucleoSpin-RNA, and cDNA was produced according to RT-PCR (Reverse Transcription PCR). Using the obtained cDNA as a template, the expression of UCA1 was quantified according to qRT-PCR employing the TaqMan probe (n=3). GAPDH was used as a reference gene. The relative expression level of UCA1 was calculated according to a comparative Ct method, using GAPDH as a reference. The results are shown in FIG. 14. As shown in FIG. 14, it was found that the expression level of UCA1 is enhanced together with virus replication in the cell lines highly expressing UCA1.

(4) Virus-producing Ability of Vaccinia Virus in KFtx Series

Figure 15:
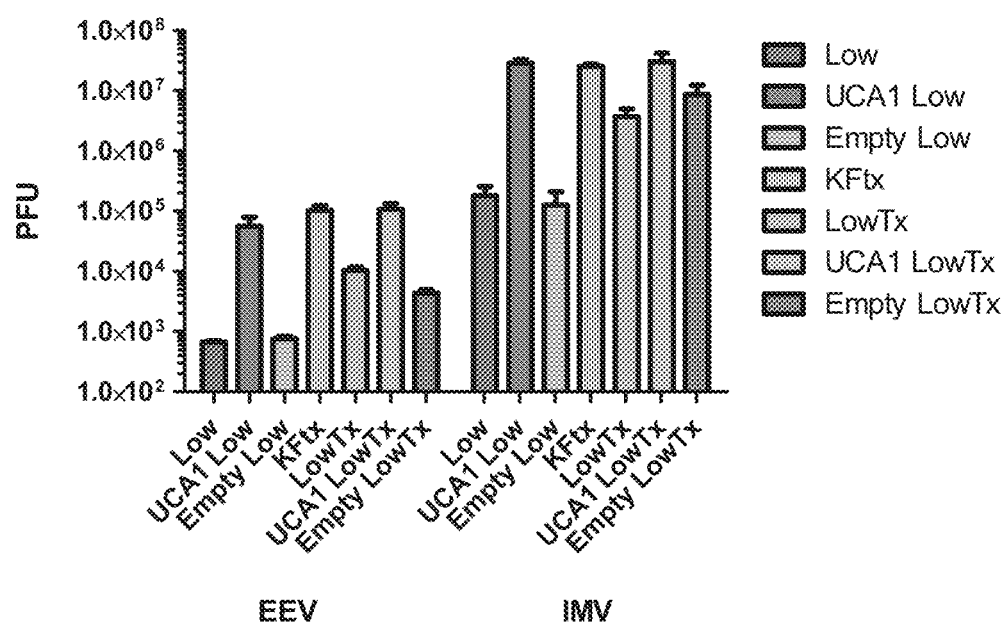
FIG. 15 shows the virus-producing ability of the vaccinia virus in the KFtx series.

Vaccinia virus has two types of infection forms, namely, IMV (intracellular mature virus) and EEV (extracellular enveloped virus). EEV has higher remote infectivity than IMV. These two types of vaccinia viruses were compared with each other in terms of production amount in the KFtx series. The KFtx series (Low, UCA1 Low, Empty Low, KFtx, LowTx, UCA1 LowTx and Empty LowTx) were seeded at a cell density of $1.5\times10^5$/well on a 6-well plate, and were then cultured at 37° C. for 36 hours. Thereafter, the cultured cells were infected with VGF+/O1L+ at MOI=0.01. The resulting cells were cultured at 37° C. for 72 hours, and thereafter, each supernatant (EEV released from the infected cells) and infected cells (IMV existing in the infected cells) were recovered. The supernatant was removed, and infected cells were then peeled using Tryple Express, followed by freezing and thawing, so as to obtain IMV. After completion of the freezing and thawing operations, sonication and centrifugation (2,000 rpm, 5 minutes) were carried out, and the obtained supernatant was recovered as a virus solution (wherein since the outer membrane structure of EEV was destructed by the freezing and thawing operations, EEV was not subjected to the steps of freezing and thawing, sonication, and centrifugation). The virus titer of each virus solution (1 ml) was measured using RK13 cells. The results are shown in FIG. 15. As shown in FIG. 15, the virus titers of EEV and IMV both corresponded to the observation images obtained under a fluorescence microscope (FIG. 12-1).

Figures 1, 16:
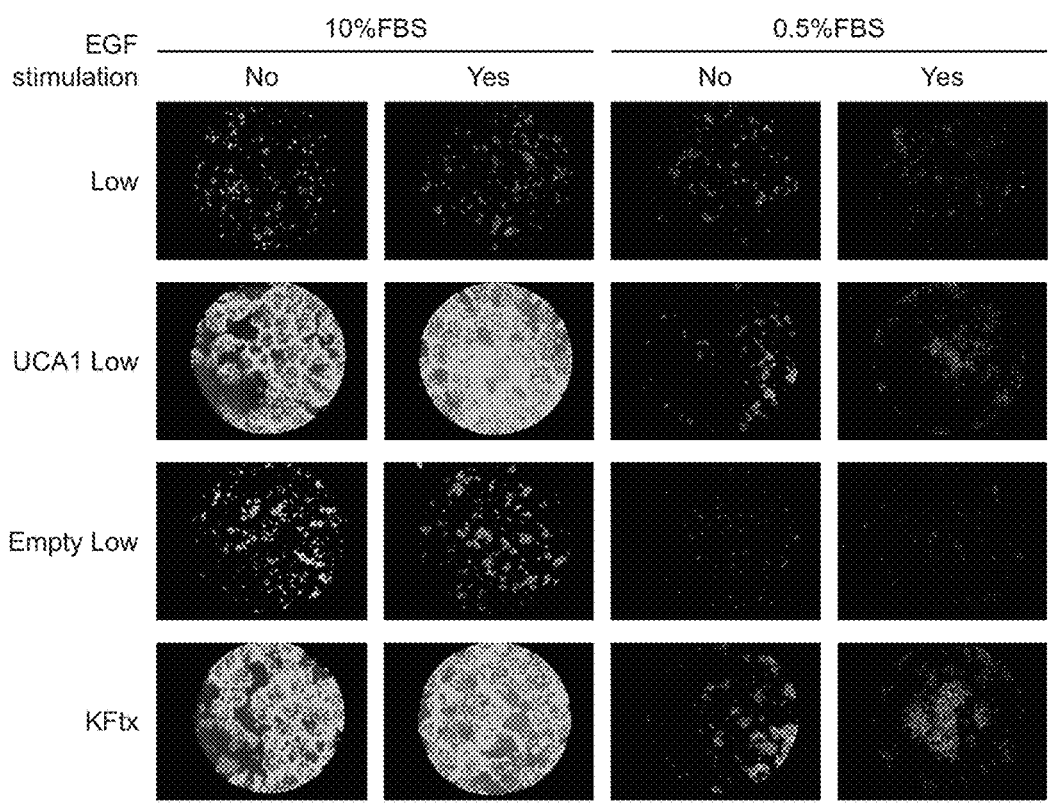
Figure 16:
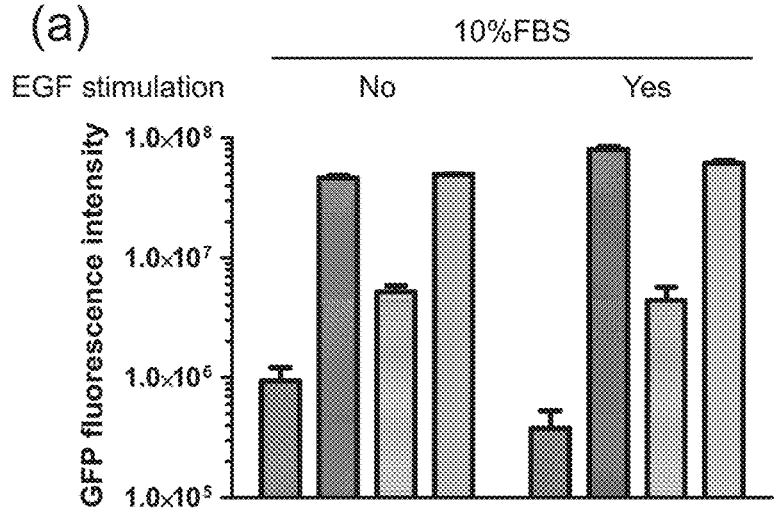
Figure 2:
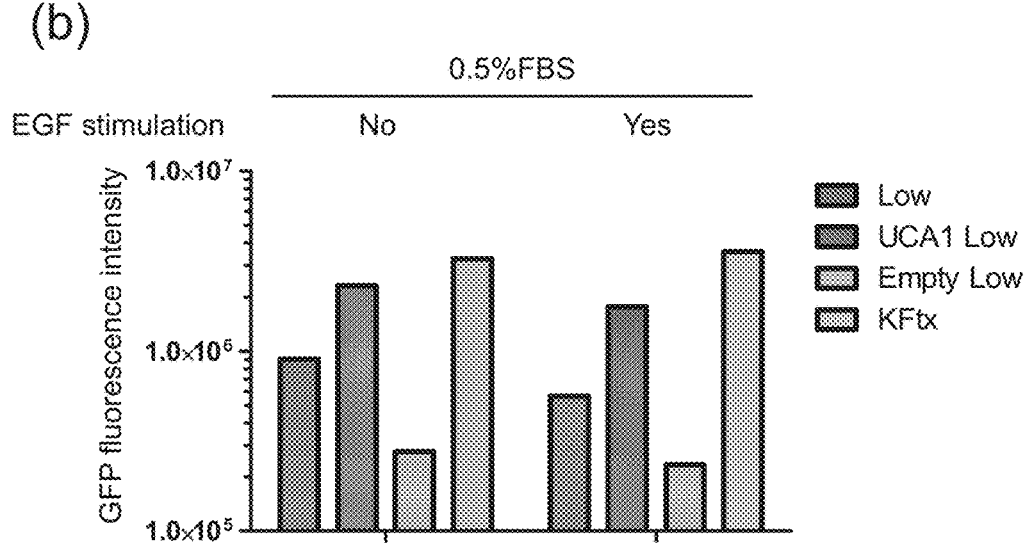
FIG. 2 shows that replication and/or propagation of a vaccinia virus depend on PTx resistance.

(5) Virus Infection Images of KFtx Series Stimulated by EGF and Quantification of Virus GFP Fluorescence A change in the replication ability of the vaccinia virus caused by activation of ERK was measured. EGFR is present upstream of the ERK, and is activated by EGF. The KFtx series (Low, UCA1 Low, Empty Low, and KFtx) were seeded at a cell density of $6\times10^3$/well on a 96-well plate, and were then cultured at 37° C. for 12 hours. Thereafter, the medium was exchanged with RPMI containing 10% FBS or 0.5% FBS. The cultured cells were further cultured at 37° C. for 24 hours, and the resulting cells were then infected with VGF+/O1L+ at MOI=0.01. Thirty minutes before the infection, the cells had been stimulated by 0.2 ng/µl EGF. Seventy-two hours after the infection, living cells were directly subjected to fluorescence observation using the Keyence fluorescence microscope BZ-X710, and at the same time, the fluorescence intensity was converted into a numerical value. The infected images are shown in FIG. 16-1, and the results of quantification of the fluorescence are shown in FIG. 16-2 (wherein FIG. 16-2A shows the results from 10% FBS, and FIG. 16-2B shows the results from 0.5% FBS). As shown with the fluorescence intensity of GFP in FIG. 16-1 and FIG. 16-2, the replication ability of the vaccinia virus was not enhanced by EGF stimulation. As given above, the enhancement of the replication ability of the vaccinia virus by ERK activation was not confirmed in the KFtx series.

(6) Change in pERK/tERK by EGF Stimulation

Figure 17:
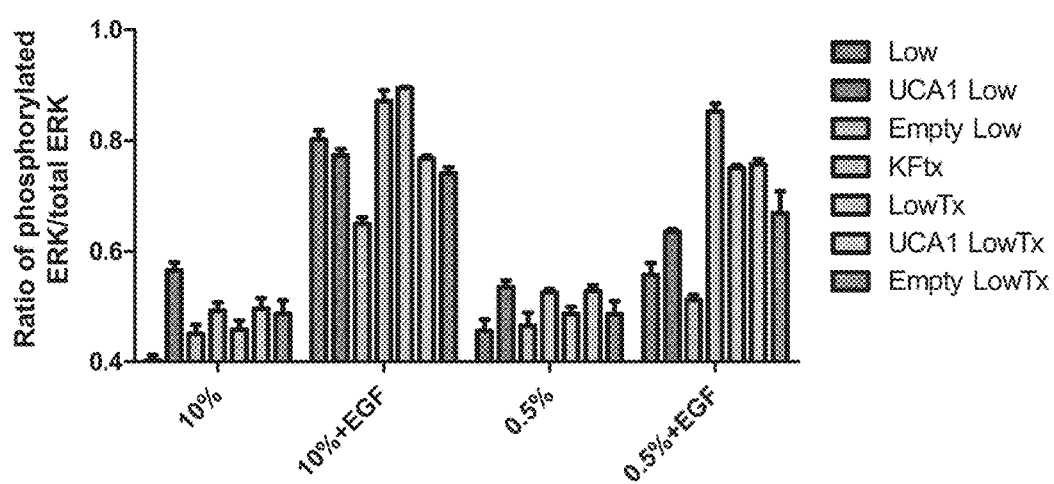
FIG. 17 shows a change in pERK/tERK by EGF stimulation.

The KFtx series (Low, UCA1 Low, Empty Low, and KFtx) were seeded at a cell density of $6\times10^3$/well in 10% FBS-containing RPMI on a 96-well plate, and were then cultured at 37° C. for 12 hours. Thereafter, the medium was exchanged with RPMI containing 10% FBS or 0.5% FBS. The cells were further cultured at 37° C. for 24 hours, and the medium was then exchanged with another one, to result in an EGF concentration of 0.2 ng/µl. After 30 minutes of EGF stimulation, tERK (total-ERK) and pERK (phosphorylated-ERK) were measured using Pierce Colorimetric In-Cell ELISA Kits (n=3). The results are shown in FIG. 17. As shown in FIG. 17, there was found no difference between 0.5% FBS and 10% FBS. In addition, it was confirmed that, in all cells, pERK was activated by EGF stimulation and the percentage of the pERK was increased.

Example 7

Figures 1, 18:
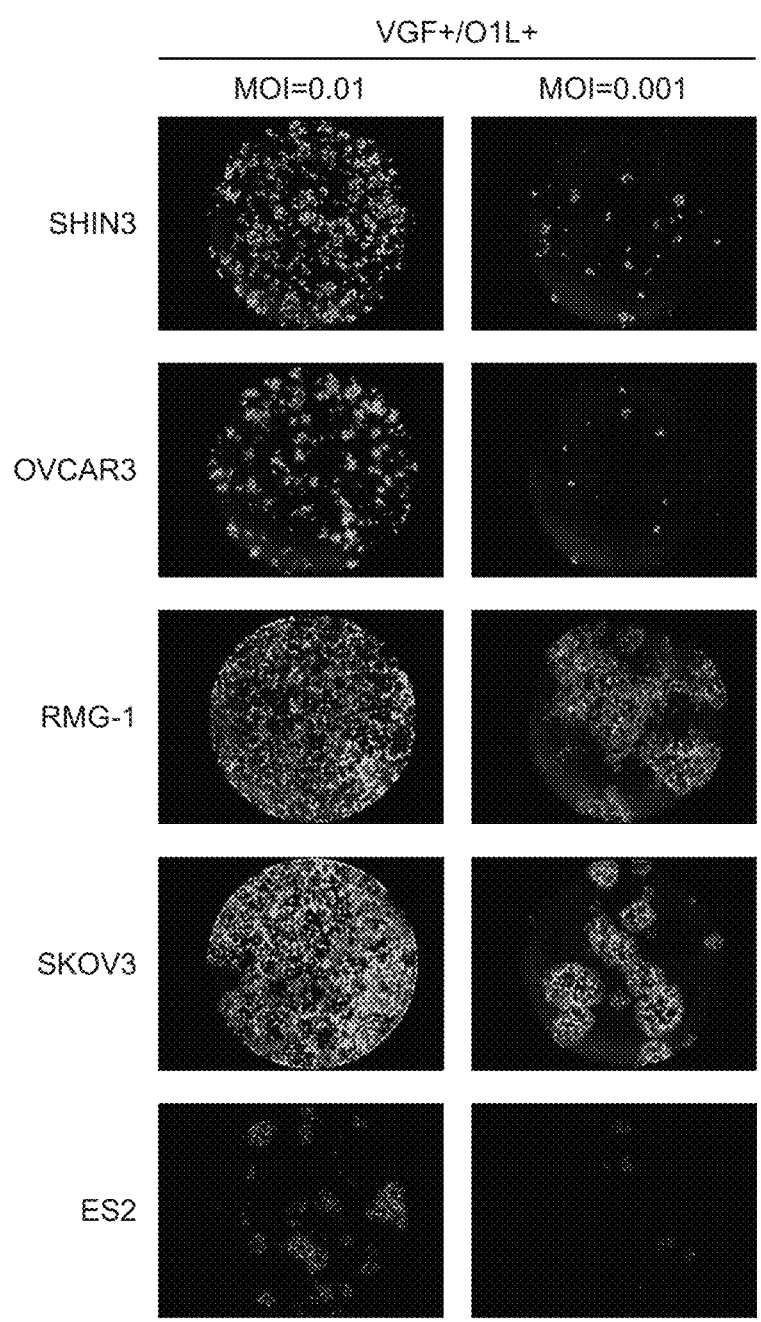
Figure 18:
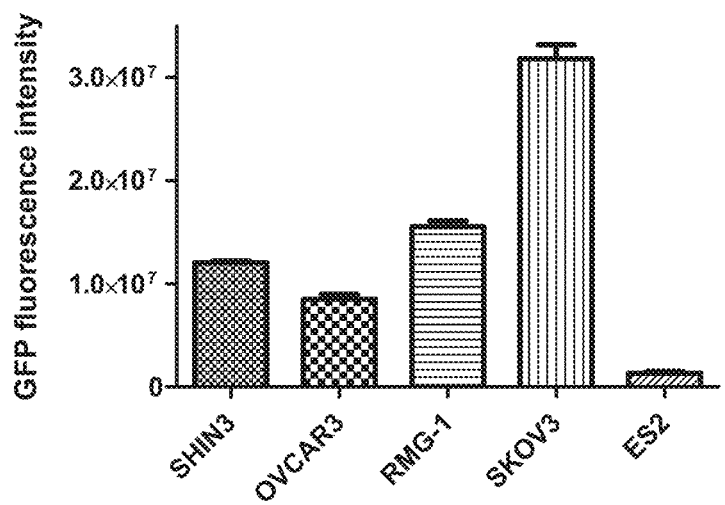
Figure 2:
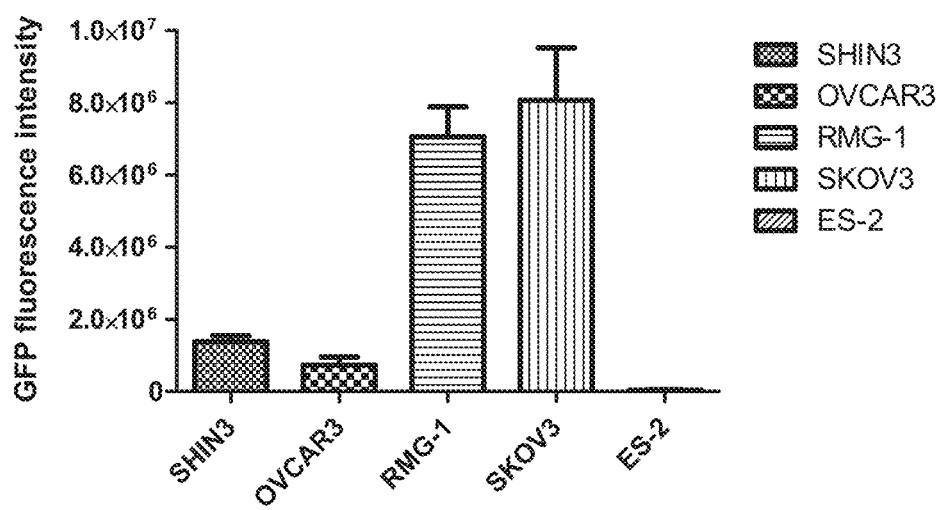

Effects of Virus in Various Ovarian Cancers (1) VGF+/O1L+ Infection Images of Various Ovarian Cancers and Quantification of Virus GFP Fluorescence Five types of ovarian cancers, namely, SHIN3, OVCAR3, RMG-1, SKOV3 and ES2 were seeded at a cell density of $1 \times 10^4$/well on a 96-well plate, and were then cultured at 37° C. for 36 hours. Thereafter, the cultured cells were infected with VGF+/O1L+ at MOI=0.01 or 0.001. The cells were cultured at 37° C. for 48 hours. Thereafter, living cells were directly subjected to fluorescence observation using the Keyence fluorescence microscope BZ-X710, and at the same time, the fluorescence intensity was converted into a numerical value. The infected images are shown in FIG. 18-1, and the results of quantification of the fluorescence are shown in FIG. 18-2 (wherein FIG. 18-2A shows the results from MOI=0.01, and FIG. 18-2B shows the results from MOI=0.001). As shown in FIG. 18-1, RMG-1 and SKOV3, in which UCA1 was highly expressed, had strong fluorescence intensity, and the replication and/or propagation ability of the virus was high. On the other hand, SHIN3, OVCAR3 and ES2, in which the expression level of UCA1 was low, had weak fluorescence intensity, and the replication and/or propagation ability of the virus was low. Moreover, as shown in FIG. 18-2, the fluorescence intensity of GFP corresponded to the observation images obtained under a fluorescence microscope.

Figures 1, 19:
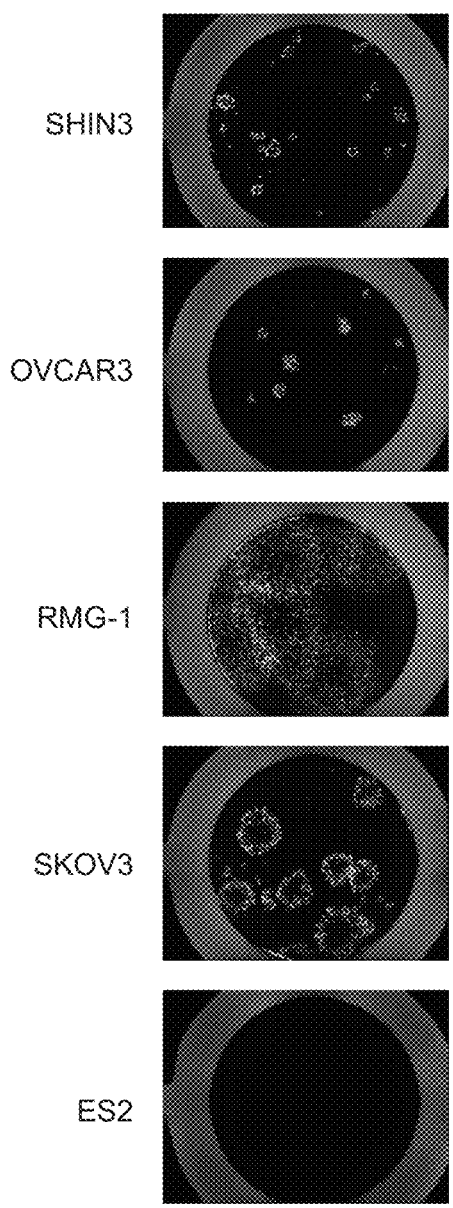
Figures 2, 19:
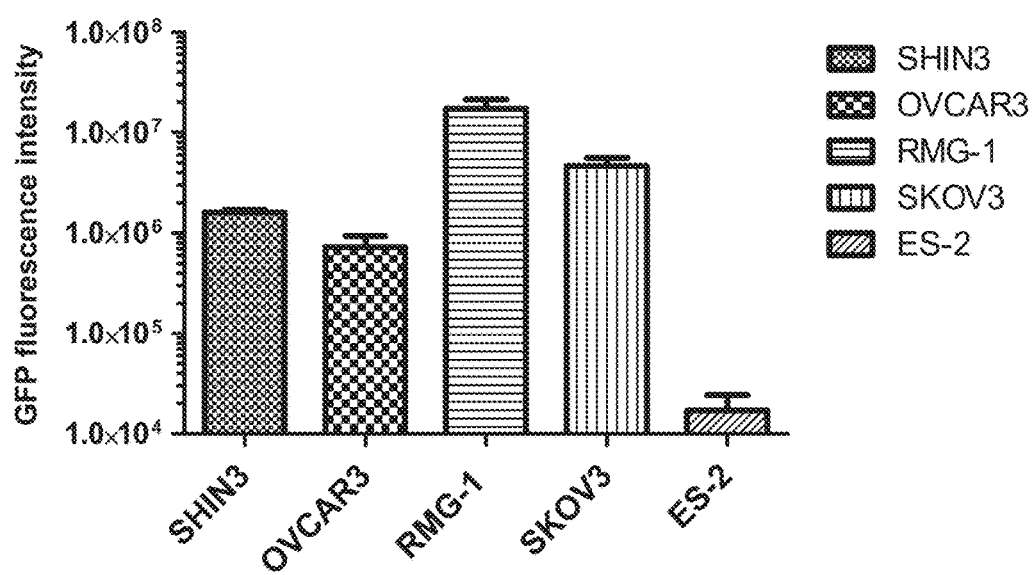

(2) VGF−/O1L− Infection Images of Various Ovarian Cancers and Quantification of Virus GFP Fluorescence Five types of ovarian cancers, namely, SHIN3, OVCAR3, RMG-1, SKOV3 and ES2 were seeded at a cell density of 0.6 to $1 \times 10^4$/well on a 96-well plate, and were then cultured at 37° C. for 36 hours. Thereafter, the cultured cells were infected with VGF−/O1L− at MOI=0.005. Thirty minutes before the infection, the cells had been stimulated by 0.2 ng/µl EGF. The cells were cultured at 37° C. for 96 hours. Thereafter, living cells were directly subjected to fluorescence observation using the Keyence fluorescence microscope BZ-X710, and at the same time, the fluorescence intensity was converted into a numerical value. The infected images are shown in FIG. 19-1, and the results of quantification of the fluorescence are shown in FIG. 19-2. As shown in FIG. 19-1, RMG-1 and SKOV3, in which UCA1 was highly expressed, had strong fluorescence intensity, and the replication and/or propagation ability of the virus was high. On the other hand, SHIN3, OVCAR3 and ES2, in which the expression level of UCA1 was low, had weak fluorescence intensity, and the replication and/or propagation ability of the virus was low. Moreover, as shown in FIG. 19-2, the fluorescence intensity of GFP corresponded to the observation images obtained under a fluorescence microscope.

Example 8

Oncolytic Property of Vaccinia Virus in KFtx Series

Figure 20:
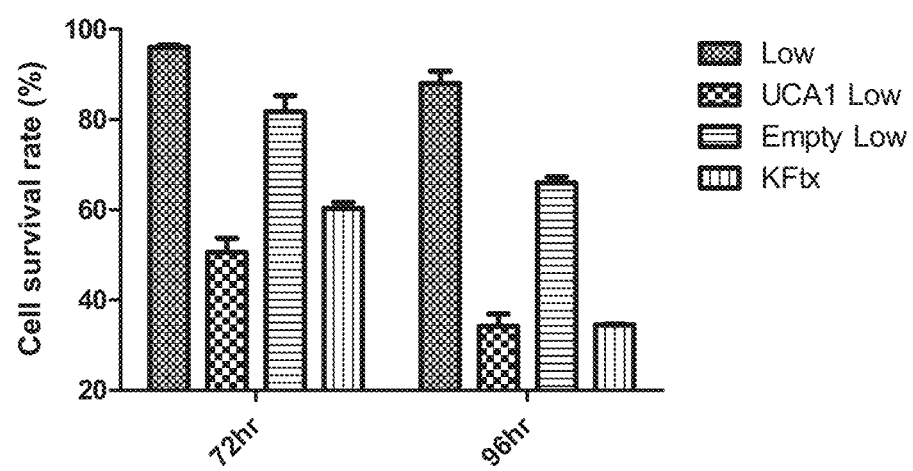
FIG. 20 shows the oncolytic property of the vaccinia virus in the KFtx series.

The KFtx series (Low, UCA1 Low, Empty Low, and KFtx) were seeded at a cell density of $6 \times 10^3$/well on a 96-well plate, and were then cultured at 37° C. for 36 hours. Thereafter, the cultured cells were infected with VGF−/O1L− at MOI=0.5. Using CellTiter 96 AQueous One Solution Cell Proliferation Assay (Promega), the number of surviving cells was measured 72 hours and 96 hours after the infection. The results are shown in FIG. 20. As shown in FIG. 20, it was demonstrated that high expression of UCA1 enhances the oncolytic property of the virus.

Example 9

Figure 21:
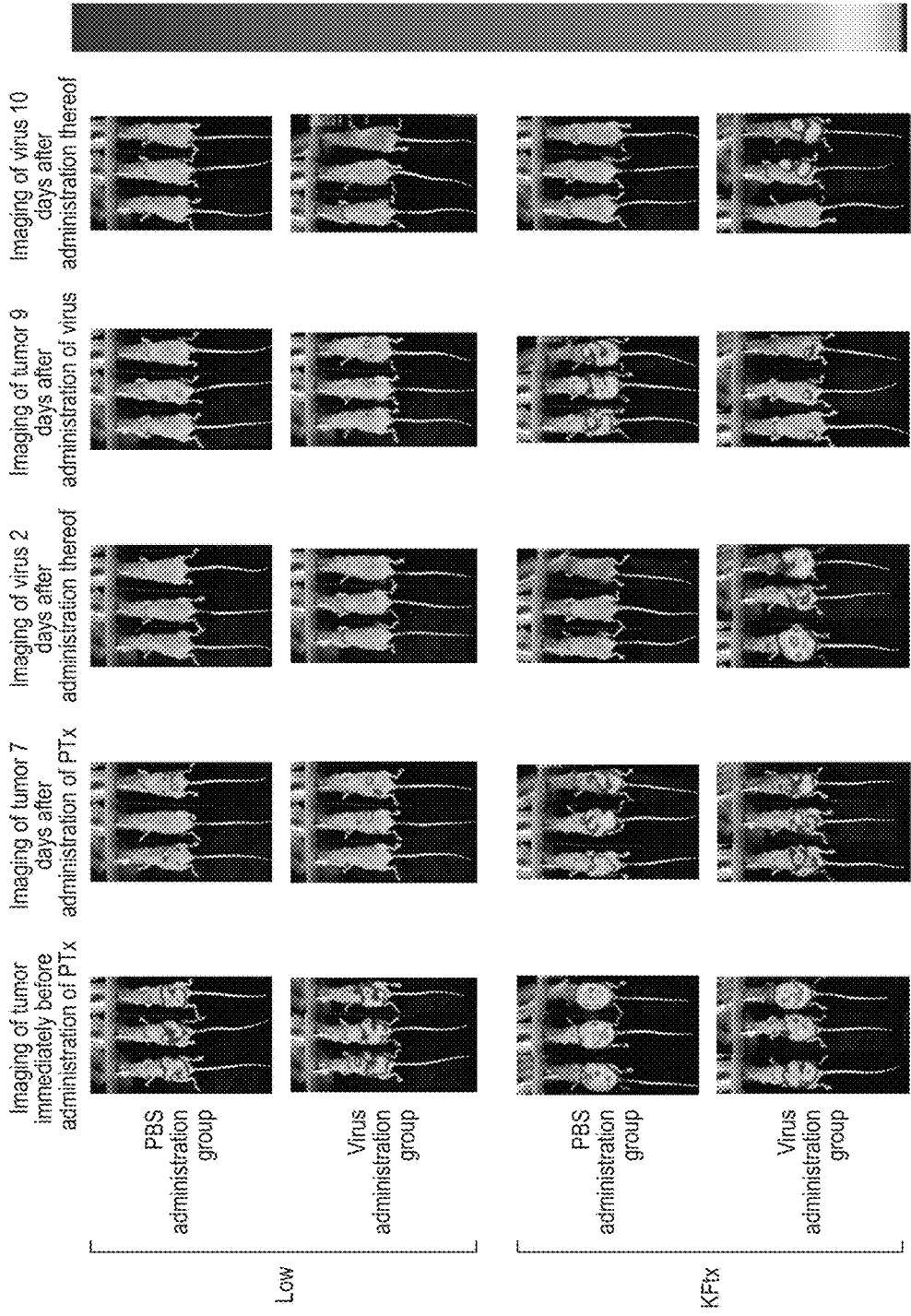
FIG. 21 shows the results of the comparison of Paclitaxel with the vaccinia virus, in terms of anticancer effects on peritoneal dissemination model mice.
Figure 22:
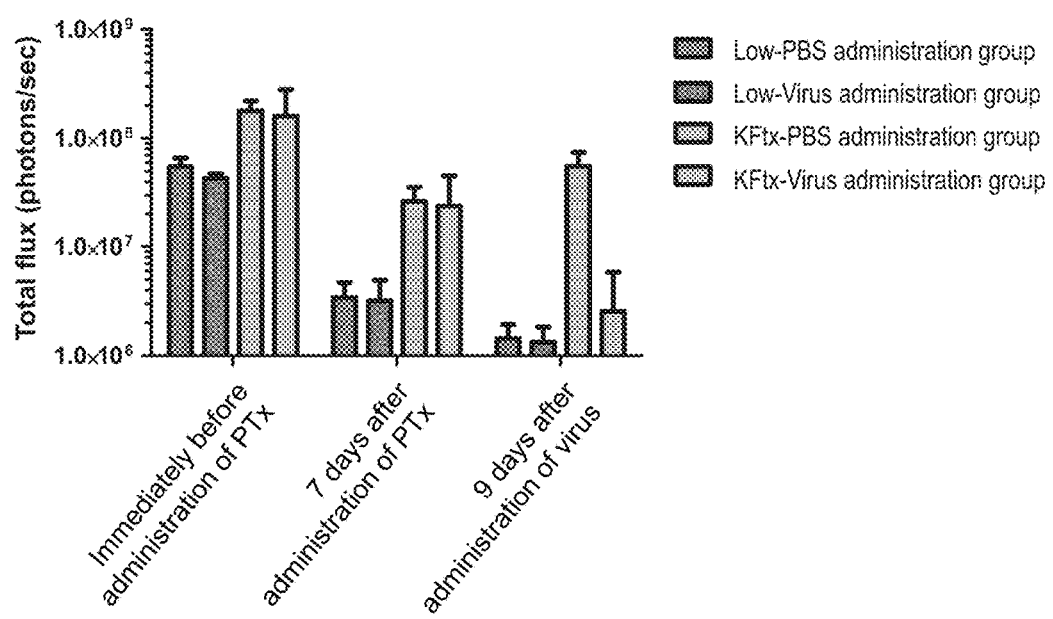
FIG. 22 shows numeric conversion of the imaging data of tumor in peritoneal dissemination model mice.

Comparison Between Anticancer Effects of Paclitaxel and Those of Virus in Peritoneal Seeding Model Mice Low cells or KFtx cells ($1 \times 10^7$), into which *Renilla* Luciferase (Rluc) had been introduced for in vive imaging, were intraperitoneally administered to BALB/cAJcl-nu/nu mice (female, 5-week-old). By intraperitoneal administration of coelenterazine as a substrate of Rluc, the engraftment of tumor in the body of mice was non-invasively confirmed using an in vive imaging system (Berthold, NightDHADE LB985). Thereafter, Paclitaxel (Pfizer) was administered to 31 mice (17 mice in a Low group, and 14 mice in a KFtx group) at a dose of 1 mg/ml/mouse. Seven days after the administration of Paclitaxel, a change in tumor signals was detected by Rluc imaging. Moreover, 8 days after the administration of Paclitaxel, VGF−/O1L− was administered to the mice at a dose of $1 \times 10^6$ pfu/200 µl/mouse, whereas 200 µl of PBS was administered to a control group (8 mice in a Low-PBS administration group, 9 mice in a Low-Virus group, 7 mice in a KFtx-PBS group, and 7 mice in a KFtx-Virus group). VGF−/O1L− expresses Firefly Luciferase (Fluc) in infected cells. Thus, by intraperitoneally administering luciferin as a substrate thereof to a mouse, virus distribution in the body of the mouse can be non-invasively visualized using an in vivo imaging system (Berthold, NightDHADE LB985). Virus distribution 2 days and 10 days after the administration of the virus was observed by Fluc imaging, and a change in the tumor growth 9 days after the administration of the virus was observed by Rluc imaging. The results are shown in FIG. 21 and FIG. 22. In FIG. 21, the right bar indicates the luminous intensity of a light source by luciferase, namely, the scale of light intensity, and it indicates the intensity of light in the order of red, orange, yellow, yellowish green, blue, and violet from the top. In FIG. 22, the total number of photons/sec as a unit indicating light intensity is shown as the longitudinal axis. As shown in FIG. 21 and FIG. 22, by the tumor imaging before administration of Paclitaxel (PTx), the engraftment of tumor was confirmed in the Low group and the KFtx group. After administration of PTx, 95% or more of KF cell-derived tumors disappeared. On the other hand, KFTx cell-derived tumors remained. From these results, it can be said that peritoneal seeding model mice, in which KFtx cells are used, can be ovarian cancer models reflecting PTx-resistant clinical images. An attempt was made to treat such remaining tumors with VGF−/O1L−. As a result, by virus imaging performed 2 days after the virus administration, high virus replication was observed in peritoneally seeded, remaining KFtx tumors. Then, by virus imaging performed 9 days after the virus administration, re-proliferation of remaining tumors was observed in the PBS administration group used as a control, whereas 98% or more of the tumors existing before the treatment with PTx disappeared in the virus administration group. Further, by virus imaging performed 10 days after the virus administration, virus replication also disappeared together with the disappearance of these tumors. On the other hand, in peritoneal seeding mice, in which Low cells were used, since almost all tumors disappeared by the action of PTx, replication of VGF−/O1L− virus having tumor-specific replication ability was not observed.

From the aforementioned results, it is suggested that therapy-resistant remaining lesions, in which UCA1 is highly expressed, can be the targets of an oncolytic vaccinia virus, and that, at the same time, UCA1 can be a biomarker for predicting anticancer effects.

INDUSTRIAL APPLICABILITY

A host regulatory factor that enhances replication and/or propagation of a vaccinia virus can be used in evaluation of the cancer therapeutic effects of the vaccinia virus and in cancer therapy.

All publications, patents and patent applications cited in the present description are incorporated herein by reference in their entirety.

Sequence Listing Free Text

SEQ ID NO: 3 Synthesized

SEQ ID NOS: 4 and 5 Primers

The invention claimed is:

1. A method for predicting and evaluating the cancer therapeutic effects of an oncolytic vaccinia virus that replicates in cancer cells, which comprises measuring the expression of a UCA1 gene in the cancer cells of a cancer patient, and then predicting that the oncolytic vaccinia virus exhibits cancer therapeutic effects on the patient, when expression of the UCA1 gene exceeds a determined threshold value.

2. The method according to claim 1, wherein the vaccinia virus is modified to allow expression of a B5R gene, and wherein the vaccinia virus is an LC16 strain, an LC16mO strain, or an LC16m8 strain.

3. The method according to claim 1, wherein the expression of the UCA1 gene is measured by RT-PCR.

4. An oncolytic vaccinia virus that replicates in cancer cells, into which a UCA1 gene has been expressibly introduced, wherein the vaccinia virus is modified to allow the expression of a B5R gene, and wherein the vaccinia virus is an LC16 strain, an LC16mO strain, or an LC16m8 strain.

5. The vaccinia virus according to claim 4, which allows the UCA1 gene to express in cancer cells and replicates in the cancer cells by regulation of UCA1.

6. A pharmaceutical composition for cancer therapy, comprising the vaccinia virus according to claim 4.

7. A pharmaceutical composition kit for cancer therapy, comprising an expression vector into which a UCA1 gene has been expressibly introduced, in combination with an oncolytic vaccinia virus that replicates in cancer cells, wherein the vaccinia virus is modified to allow the expression of a B5R gene, and wherein the vaccinia virus is an LC16 strain, an LC16mO strain, or an LC16m8 strain.

* * * * *

SEQUENCE LISTING

```
<160> NUMBER OF SEQ ID NOS: 5

<210> SEQ ID NO 1
<211> LENGTH: 2314
<212> TYPE: DNA
<213> ORGANISM: Homo sapiens

<400> SEQUENCE: 1
tgacattctt ctggacaatg agtcccatca tctctccacc atgcaccttg tgactccctc      60
ctctgctgac aacagataac caccttaac tgtaactttc cacagcctac cccagcccta     120
taaagctgcc cctctcctat ctcccttcgc tgactctctt ttcagactca gcccacttgc     180
acccaagtga attaacagcc ttgttgctca cacaaagcct gtttaggtgg tcttctatac     240
ggacatgctt gacacttggt gccaaaatct gggccagggg gactccttcg tgagaccggc     300
cccctgtcct ggccctcatt ccgtgaagag atccacctgc gacctcgggt cctcagacca     360
gcccaaggaa catctcacca atttcaaatc ggatctcctc ggcttagtgg ctgaagactg     420
atgctgcccg atcgcctcag aagcccttg gaccatcaca gatgccgagc ttcgggtaac     480
tcttacggtg gaggattccc agccatatga agacaccta gctggacgat cagtccttgt     540
caaaagtctg acccctcaaa ctctacagcc tcaatggacc agaccctacc cggtcattta     600
tagcacacca actgccgtcc atctgcagga ccctctccat tgggttcacc attccagaat     660
aaagccatgc ccatcagaca gccagcttga tctctcctct tcctcctgga agccacaaga     720
ttaggccgag agccgatcag acaaacaacc tacaacctt aagctcctgg cagcgcccag     780
ccaaggccat gcttccatgc aacactcctt ccaaatggcc atcccagcat gcttccaagc     840
aggcttcatc cgttcctctg gaccctcatc tcttaagacc tgccgcctat aaaaaggatt     900
atatcttgag accctatcct ctaaaatttt ttccacaccc aaaacaaaaa atctctgggt     960
caaaagtcta aaacgcttag gctggcaacc atcagatcct tgcccatggt gtcctcaagc    1020
ctactctcat gaaatggaca acagtacacg catatggggc cagttccaca tatttggcaa    1080
ccagaccagc atccaggaca acacaaagta tgttgtttgt tgttagaggg cttgggacat    1140
ttcactcttt gccagcctca gcttaatcca ggagacaaag attattttcc ttattatctc    1200
ttctgcatag gatctgcaat cagaactatt gaacttctcc attcagaccg ccactcacac    1260
ctatgggaaa agggtaatgt atcatcggct tagcaacagg gaatactatt cgtatgatgg    1320
aaaatgggga caaaaggctt tggtacataa aacattattc cttccttggc ctaaaaactc    1380
atcgccacct acattaaagc taatatgcct gattactgtt tttagagaac ttattttatt    1440
```

```
aggggcagttc caagctcaaa aatacgctaa ctggcacctt gttagctaca taaaaatgca    1500
ccctagaccc gaaacttact agactcatta taaaattttc tttaaggtgt ccacgcagtc    1560
cctggtcaca cttgaagcag tccggagaaa tatcagccct accccagtaa tccccagaag    1620
gaacttacac tttttttaa tcttttccta caacttcata ttttataaat aaaaagacaa    1680
aaatgtcagg cctgtgagct gaagcttagc cattgtaacc cctgtgacct gcacatatcc    1740
gtccaggtgg cctgcaggag ccaagaagtc tggagcagcc gaaaaaccac aaagaagtga    1800
aacagccagt tcctgcctta actaattaac ccaccttacg acattccacc attatgactt    1860
gtccaccatt atgacttgtt cctgccctgc cccaactgat caatcaaccc tgtgacattc    1920
ttctcctgga caatgagtcc catcatctct ccaccatgca ccttgtgacc ccctcctctg    1980
ctgaggataa ccacctttaa ctgtaacttt ccacgcctac ccaagcccta taaagctgcc    2040
cctctcctat ctcccttcac tgactctctt ttcggactca gcccacttgc acccaagtga    2100
attaacagcc ttgttgctca cacaaagcct gattgggtgt cttctatacg acacgcgtg    2160 acaggaacct caacccaaag gcagtctgat gaggtgtcta agataaaagt agcggcacaa    2220
aggcttttgt aaacagaggc gtttcatgtg gttttccttt cctttcctta tatgtgaaaa    2280
ggtgacagaa aagaaatctt cctaaaagag tcag                                2314
```

<210> SEQ ID NO 2
<211> LENGTH: 1409
<212> TYPE: DNA
<213> ORGANISM: Homo sapiens

<400> SEQUENCE: 2

```
tgacattctt ctggacaatg agtcccatca tctctccacc atgcaccttg tgactccctc      60
ctctgctgac aacagataac cacctttaac tgtaactttc cacagcctac cccagcccta    120
taaagctgcc tctctcctat ctcccttcgc tgactctctt ttcagactca gcccacttgc    180
acccaagtga attaacagcc ttgttgctca cacaaagcct gtttaggtgg tcttctatat    240
ggacatgcgt gacacttggt gccaaaatct gggccagggg gactcctttg tgagaccggc    300
cccctgtcct ggccctcact ccgtgaagag atccacctgc gacctcgggt cctcagacca    360
gcccaaggaa catctcacca atttcaaatc ggatctcctc ggcttagtgg ctgaagactg    420
atgctgcccg atcgcctcag aagcccctg gaccatcaca gatgccgagc ttcgggtaac    480
tcttacggtg gaggattccc agccatatga agacacccta gctggacgat cagtccttgt    540
caaaagtctg accccctcaaa ctctacagcc tcaatggacc agaccctacc cggtcattta    600
tagcacacca actgccgtcc atctgcagga ccctctccat tgggttcacc attccagaat    660
aaagccatgc ccatcagaca gccagcttga tctctcctct tcctcctgga agccacaaga    720
ttaggccgag agccgatcag acaaacaacc tacaacccttt aagctcctgg cagcgcccag    780
ccaaggccat gcttccatgc aacactcctt ccaaatggcc atcccagcat gcttccaagc    840
aggcttcatc cgttcctctg gaccctcatc tcttaagacc tgccgcctat aaaaaggatt    900
atatcttgag accctatcct ctaaaatttt ttccacaccc aaaacaaaaa atctctgggt    960
caaaagtcta aacgcttag gctggcaacc atcagatcct tgcccatggt gtcctcaagc   1020
ctactctcat gaaatggaca acagtacacg catatggggc cagctccaca tatttggcaa   1080
ccagaccagc atccaggaca acacaaagta tgttgtttgt tgttagaggg cttgggacat   1140
ttcactcttt gccagcctca gcttaatcca ggagacaaag attatttttcc ttattatctc   1200
```

| | |
|---|---:|
| ttctgcatag gatctgcaat cagaactatt gaacttctcc attcagaccg ccactcacac | 1260 |
| ctatgggaaa agggtaatgt atcatcggct tagcaacagg gaatactatt cgtatgatgg | 1320 |
| aaaatgggga caaaaggctt tggtacataa acattattc cttccttggc ctaaaaactc | 1380 |
| atcgccacct acattaaagc taatatgcc | 1409 |

<210> SEQ ID NO 3
<211> LENGTH: 1420
<212> TYPE: DNA
<213> ORGANISM: Artificial
<220> FEATURE:
<223> OTHER INFORMATION: Synthetic

<400> SEQUENCE: 3

| | |
|---|---:|
| ggatcctgac attcttctgg acaatgagtc ccatcatctc tccaccatgc accttgtgac | 60 |
| tccctcctct gctgacaaca gataaccacc tttaactgta actttccaca gcctacccca | 120 |
| gccctataaa gctgccctc tcctatctcc cttcgctgac tctcttttca gactcagccc | 180 |
| acttgcaccc aagtgaatta acagccttgt tgctcacaca aagcctgttt aggtggtctt | 240 |
| ctatacggac atgcttgaca cttggtgcca aaatctgggc caggggact ccttcgtgag | 300 |
| accggccccc tgtcctggcc ctcattccgt gaagagatcc acctgcgacc tcgggtcctc | 360 |
| agaccagccc aaggaacatc tcaccaattt caaatcggat ctcctcggct tagtggctga | 420 |
| agactgatgc tgcccgatcg cctcagaagc cccttggacc atcacagatg ccgagcttcg | 480 |
| ggtaactctt acgtggagg attcccagcc atatgaagac ccctagctg gacgatcagt | 540 |
| ccttgtcaaa agtctgaccc ctcaaactct acagcctcaa tggaccagac cctaccggt | 600 |
| catttatagc acaccaactg ccgtccatct gcaggaccct ctccattggg ttcaccattc | 660 |
| cagaataaag ccatgcccat cagacagcca gcttgatctc tcctcttcct cctggaagcc | 720 |
| acaagattag gccgagagcc gatcagacaa acaacctaca acccttaagc tcctggcagc | 780 |
| gcccagccaa ggccatgctt ccttgcaaca ctccttccaa atggccatcc cagcatgctt | 840 |
| ccaagcaggc ttcatccgtt cctctggacc ctcatctctt aagacctgcc gcctataaaa | 900 |
| aggattatat cttgagaccc tatcctctaa aattttttcc acacccaaaa caaaaaatct | 960 |
| ctgggtcaaa agtctaaaac gcttaggctg gcaaccatca gatccttgcc catggtgtcc | 1020 |
| tcaagcctac tctcatgaaa tggacaacag tacacgcata tggggccagt tccacatatt | 1080 |
| tggcaaccag accagcatcc aggacaacac aaagtatgtt gtttgttgtt agagggcttg | 1140 |
| ggacatttca ctctttgcca gcctcagctt aatccaggag acaaagatta ttttccttat | 1200 |
| tatctcttct gcataggatc tgcaatcaga actattgaac ttctccattc agaccgccac | 1260 |
| tcacacctat gggaaaggg taatgtatca tcggcttagc aacagggaat actattcgta | 1320 |
| tgatggaaaa tggggacaaa aggctttggt acataaaaca ttattccttc cttggcctaa | 1380 |
| aaactcatcg ccacctacat taaagctaat atgcggccgc | 1420 |

<210> SEQ ID NO 4
<211> LENGTH: 30
<212> TYPE: DNA
<213> ORGANISM: Artificial
<220> FEATURE:
<223> OTHER INFORMATION: Primer

<400> SEQUENCE: 4

| | |
|---|---:|
| ctggatcctg acattcttct ggacaatgag | 30 |

```
<210> SEQ ID NO 5
<211> LENGTH: 33
<212> TYPE: DNA
<213> ORGANISM: Artificial
<220> FEATURE:
<223> OTHER INFORMATION: Primer

<400> SEQUENCE: 5
ctgcggccgc atattagctt taatgtaggt ggc                            33
```